United States Patent
Timm et al.

(10) Patent No.: US 10,034,721 B1
(45) Date of Patent: Jul. 31, 2018

(54) ROBOTIC ARM CART HAVING SHOCK ABSORBING MECHANISMS AND USES THEREFOR

(71) Applicant: Verb Surgical Inc., Mountain View, CA (US)

(72) Inventors: Richard William Timm, Cincinnati, OH (US); Seung Mo Lim, Santa Cruz, CA (US); Robert T. Wiggers, Belmont, CA (US); Bernard Fai Kin Siu, San Jose, CA (US); Karen Shakespear Koenig, San Jose, CA (US)

(73) Assignee: Verb Surgical Inc., Mountain View, CA (US)

( * ) Notice: Subject to any disclaimer, the term of this patent is extended or adjusted under 35 U.S.C. 154(b) by 0 days.

(21) Appl. No.: 15/717,599

(22) Filed: Sep. 27, 2017

(51) Int. Cl.
| | |
|---|---|
| A61B 50/13 | (2016.01) |
| A61B 90/50 | (2016.01) |
| B62B 5/00 | (2006.01) |
| B62B 3/04 | (2006.01) |
| B62B 3/02 | (2006.01) |
| A61B 90/00 | (2016.01) |
| A61B 34/30 | (2016.01) |

(52) U.S. Cl.
CPC ............ *A61B 50/13* (2016.02); *A61B 90/50* (2016.02); *B62B 3/02* (2013.01); *B62B 3/04* (2013.01); *B62B 5/0006* (2013.01); *A61B 34/30* (2016.02); *A61B 2090/034* (2016.02)

(58) Field of Classification Search
CPC .......... A61B 50/13; A61B 90/50; A61B 34/30
See application file for complete search history.

(56) References Cited

U.S. PATENT DOCUMENTS

| | | | | |
|---|---|---|---|---|
| 9,694,839 | B2* | 7/2017 | Canady | B62B 3/04 |
| 2009/0240370 | A1* | 9/2009 | Nichols | B01L 3/565 |
| | | | | 700/248 |
| 2009/0248041 | A1* | 10/2009 | Williams | A61B 8/12 |
| | | | | 606/130 |
| 2013/0085389 | A1* | 4/2013 | Tsang | A61B 8/12 |
| | | | | 600/442 |
| 2014/0052154 | A1* | 2/2014 | Griffiths | B25J 9/1633 |
| | | | | 606/130 |
| 2014/0276949 | A1* | 9/2014 | Staunton | A61B 17/32002 |
| | | | | 606/130 |

(Continued)

*Primary Examiner* — Erez Gurari
(74) *Attorney, Agent, or Firm* — Womble Bond Dickinson (US) LLP

(57) ABSTRACT

Apparatuses and methods described herein relate to arm carts for transporting and coupling a robotic arm to a surgical table. In some embodiments, an arm cart may include a damping mechanism (e.g., a spring, a dashpot) configured to damp an impact force imparted to the robotic arm due to the arm contacting another object, such as a surgical table. In other embodiments, an arm cart may include a backstop with an inclined surface configured to damp an impact force imparted to the robotic arm. In other embodiments, the arm cart may include a compliant arm support that is bendable to damp an impact force imparted to a robotic arm. In some embodiments, the arm cart may include a damping mechanism configured to move from an extended position to a retracted position to permit a robotic arm to couple to a surgical table.

20 Claims, 14 Drawing Sheets

(56) References Cited

U.S. PATENT DOCUMENTS

| | | | |
|---|---|---|---|
| 2016/0076992 A1* | 3/2016 | Gillespie | G01N 21/01 |
| | | | 356/244 |
| 2017/0000575 A1* | 1/2017 | Griffiths | A61B 34/25 |
| 2017/0065355 A1* | 3/2017 | Ross | A61B 34/30 |
| 2017/0071693 A1* | 3/2017 | Taylor | A61B 90/50 |
| 2017/0119421 A1* | 5/2017 | Staunton | A61B 17/32002 |
| 2017/0312047 A1* | 11/2017 | Swarup | A61B 90/50 |
| 2018/0042682 A1* | 2/2018 | Iceman | A61B 34/20 |

\* cited by examiner

ROBOTIC ARM CART HAVING SHOCK ABSORBING MECHANISMS AND USES THEREFOR

BACKGROUND

Embodiments described herein relate to apparatuses and methods for a robotic arm cart for transporting, delivering, and securing robotic arms to, for example, a surgical table.

In surgical robotic systems, robotic arms can be coupled to a patient operating table. Once coupled, the robotic arms can assist with manipulating instruments based on commands from an operator. For example, in response to operator commands, a robotic arm having multiple degrees of freedom can move a surgical instrument in order to perform an operation on a patient. Robotic arms, however, may be sensitive to contact and easily damaged. When one or more robotic arms are loaded together on a cart, the cart may also be heavy and can pick up a substantial amount of momentum during transportation such that it may not be easy for a user to steer the cart to avoid objects and/or to slow down the cart when approaching the operating table. In such instances, if the robotic arm contacts the operating table or some other object at a high velocity, the robotic arm and/or the operating table may become damaged due shock or impact forces resulting from the contact. When a robotic arm becomes damaged, it is often difficult and costly to repair and may also cause significant delays in surgical operations. Thus, additional apparatuses and methods for protecting a robotic arm from damage during transport and/or attachment of the arm to an operating table are desirable.

SUMMARY

Apparatuses and methods for providing a robotic arm cart for transporting, delivering, and securing robotic arms to a surgical table having a table top on which a patient can be disposed are described herein. In some embodiments, a robotic arm cart having an arm support with an engagement feature and a damping mechanism may be provided. The cart may have a base that is freely moveable relative to a surgical table. The arm support may be coupled to the base and releasably coupled to robotic arm. The arm support may be configured to support the arm in a position in which a portion of the arm is exposed to contact the surgical table. The engagement feature of the arm support may be engageable with a portion of the arm, and the damping mechanism of the arm support may be configured to damp an impact force imparted to the arm by the surgical table when the base is moved to a location proximate to the surgical table and the arm contacts the surgical table. In specific embodiments, the damping mechanism may be a spring or a dashpot.

In some embodiments, a method of coupling a robotic arm to a surgical table may include moving a surgical robotic arm from a stored position to a deployed position, moving a cart supporting the arm to a location proximate to a surgical table in which the arm contacts the surgical table, damping an impact force imparted to the arm by the surgical table when the arm contacts the surgical table, and coupling a coupler of the arm to a coupling site of the surgical table. Moving the arm from the stored position to the deployed position may include rotating a portion of an arm support releasably coupled to the arm about a pivot point. In specific embodiments, damping the impact force may include compressing a linear spring in a first direction, and in other embodiments, damping the impact force may include displacing a compressing member of a dashpot.

In some embodiments, a robotic arm cart including multiple arm supports and a backstop disposed on one of the arm supports for damping an impact force transferred to the robotic arm may be provided. The cart may have a base that is freely moveable relative to a surgical table. The multiple arm supports may include a first arm support and a second arm support that are each coupled to the base. The first and second arm supports may be configured to support the arm such that a portion of the arm is exposed to contact the surgical table. The first and second arm support may also be configured to permit movement of the arm between a first position in which a center of gravity of the arm is disposed below the first arm support and a second position in which the center of gravity of the arm is disposed above the first arm support. The cart may also have a backstop that is disposed on the second arm support and configured to damp an impact force imparted to the arm by the surgical table when the base is moved to a location proximate to the surgical table and the arm contacts the surgical table.

In some embodiments, a method of coupling a robotic arm to a surgical table may include moving a cart supporting a surgical robotic arm to a location proximate to the surgical table in which the arm contacts the surgical table, damping an impact force imparted to the arm by the surgical table when the arm contacts the surgical table, and coupling a coupler of the arm to a coupling site of the surgical table. Once the coupler is coupled to the coupling site, the arm may be moved from a first position in which the center of gravity of the arm is disposed below a portion of the cart and the cart is not separable from the arm to a second position in which the center of gravity of the arm is disposed above the portion of the cart and the cart is separable from the arm. The cart then may be moved away from the location proximate to the surgical table.

In some embodiments, a robotic arm cart including a compliant or bendable arm support is provided. The cart may have a base that is freely moveable relative to a surgical table. The arm support may be configured to support the arm such that a portion of the arm is exposed to contact the surgical table. The arm support may also be bendable such that it can damp an impact force imparted to the arm by the surgical table when the base is moved to a location proximate to the surgical table and the arm contacts the surgical table. In specific embodiments, the arm support is flexible in a plane transverse to a longitudinal axis of the arm support and rigid along the longitudinal axis of the arm support. In specific embodiments, the arm support may include a flexible bellows that enables the arm support to bend.

In some embodiments, a method of coupling a robotic arm to a surgical table may include moving a cart supporting a surgical robotic arm to a location proximate to the surgical table in which the arm contacts the surgical table, damping an impact force imparted to the arm by the surgical table when the arm contacts the surgical table, and coupling a coupler of the arm to a coupling site of the surgical table. Damping the impact force may include bending an arm support coupled to the cart and releasably coupled to the arm such that the arm translates and rotates relative to the cart when the arm contacts the surgical table, and transferring a portion of the impact force from the arm to the cart.

In some embodiments, a robotic arm cart including a damping mechanism coupled to a base and moveable between an extended positon to a retracted positon may be provided. The base of the cart may be freely moveable on a support surface relative to a surgical table, and the damping mechanism may extend from a front side of the base such that it is configured to contact the surgical table when the base is moved to a location proximate to the surgical table. The damping mechanism may be capable of damping an impact force imparted to the damping mechanism by the surgical table when the damping mechanism contacts the surgical table. The damping mechanism may also be movable from the extended position to the retracted position to permit a coupler of the arm to couple to a coupling site of the surgical table. In specific embodiments, the damping mechanism may include a bumper component configured to contact the surgical table and an energy-absorbing component configured to damp the impact force. In specific embodiments, the cart may also include an arm support releasably coupled to the arm and configured to move the arm between a first position in which the coupler is not engageable with the coupling site and a second position in which the coupler is engageable with the coupling site, where the arm support is designed to move the arm from the first position to the second position when the damping mechanism moves from the extended position to the retracted position.

In some embodiments, a method of coupling a robotic arm to a surgical table may include moving a cart supporting a surgical robotic arm to a location proximate to the surgical table in which a damping mechanism extending from the cart contacts the surgical table, damping an impact force imparted to the damping mechanism by the surgical table, further moving the cart toward the surgical table at a velocity below a predefined velocity such that the damping mechanism moves from an extended position in which the damping mechanism prevents a coupler of the arm from coupling to a coupling site of the surgical table to a retracted position in which the damping mechanism permits the coupler to couple to the coupling site, and coupling the coupler to the coupling site. In specific embodiments, moving the damping mechanism from the extended position to the retracted position includes linearly displacing the damping mechanism, and in other embodiments, moving the damping mechanism from the extended position to the retracted position includes rotating the damping mechanism.

DETAILED DESCRIPTION

Apparatuses and methods for providing a robotic arm cart for transporting, delivering, and securing robotic arms to a surgical table having a table top on which a patient can be disposed are described herein. These apparatuses and methods can include a cart that protects one or more robotic arms from being damaged during transport and attachment of the robotic arms to a surgical table. The cart can include, for example, a damping mechanism that reduces or damps an impact force imparted to a robotic arm (e.g., absorbs shock imparted to the robotic arm) as a result of the robotic arm coming into contact with the surgical table or some other object.

In some embodiments, an apparatus includes an arm cart including an arm container and a base. The arm container can be configured to receive and contain one or more robotic arms. The arm cart can include a first coupling member configured to engage with a second coupling member associated with a surgical table such that, when the first coupling member is engaged with the second coupling member, the one or more robotic arms can be releasably coupled with the surgical table. The arm cart can provide for movement of one or more robotic arms in at least one of a lateral, longitudinal, or vertical direction relative to the table top prior to the securement of the one or more robotic arms to the surgical table.

Figure 1A:
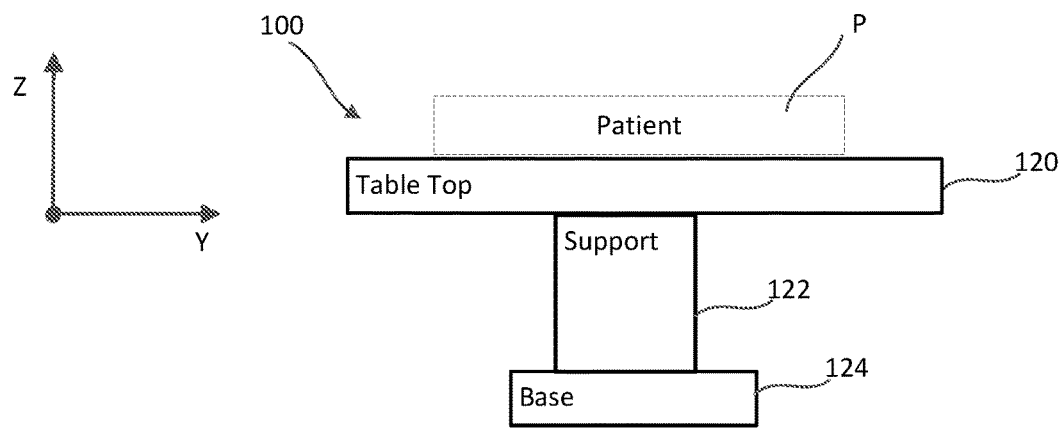
FIGS. 1A and 1B are a schematic side view and a schematic top view, respectively, of a surgical table, according to an embodiment.
Figure 1B:
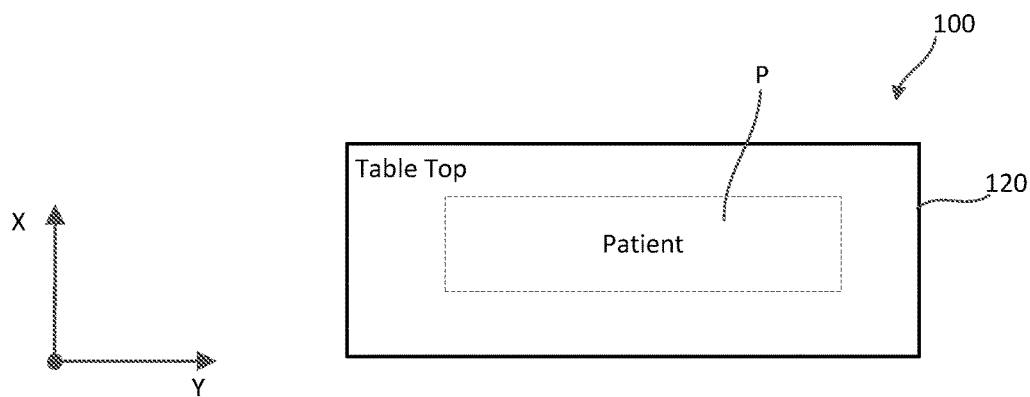

As shown schematically in FIGS. 1A-1B, a surgical table 100 includes a table top 120, a table support 122 and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a "pedestal") may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axes. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top may be mounted to the base 124, which can be fixed to the floor of the operating room, or can be movable relative to the floor, e.g., by use of wheels on the base 124. In some embodiments, the height of the arm support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
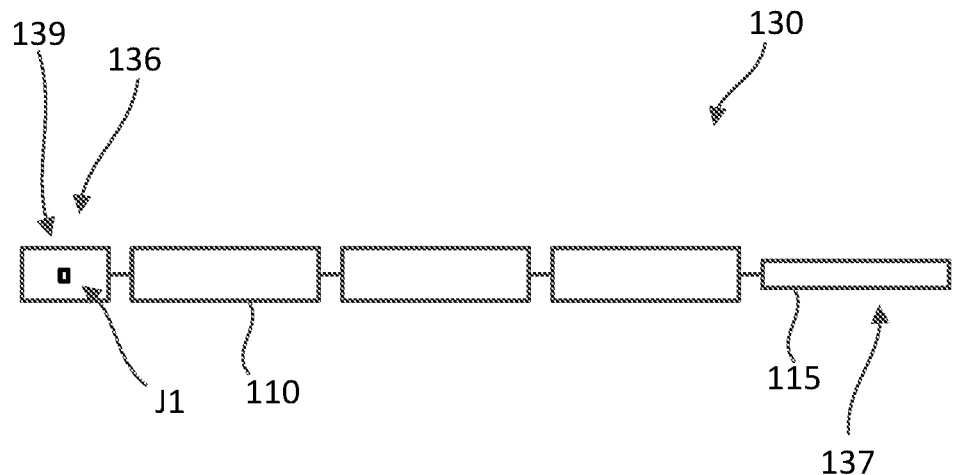
FIG. 1C is a schematic side view of a robotic arm, according to an embodiment, shown in an extended or use configuration.
Figure 1D:
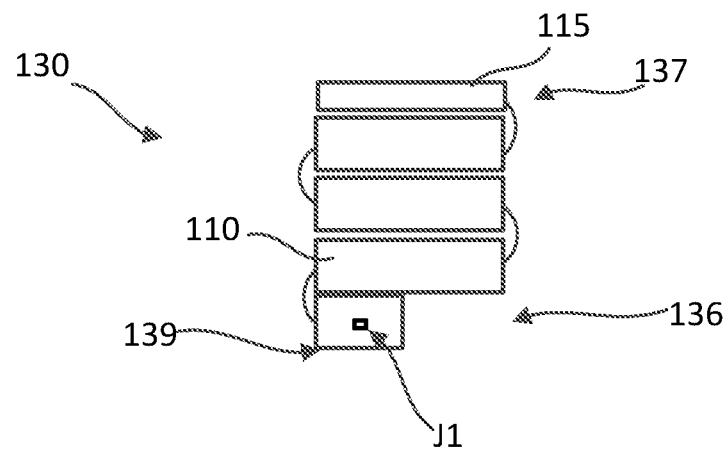
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139 (also referred to as a coupler herein). The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can provide a pivot joint to allow a distal segment of the robotic arm 130 to pivot relative to the table 100. The robotic arm 130 can be moved between various extended configurations for use during a surgical procedure, as shown in FIG. 1C, and various folded or collapsed configurations for storage when not in use, as shown in FIG. 1D.

FIGS. 2A-11 illustrate various embodiments describing apparatuses and methods for transporting, delivering, and securing a robotic arm to a surgical table. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. In some embodiments, the robotic arms 230 can be permanently or releasably coupled, in a fixed or movable location, to an arm adapter that is coupled to or separate from the surgical table. For example, as shown schematically in FIG. 2B, an arm adapter 246 can be coupled to or separate from but engageable with or coupleable to the table top 220. The robotic arms 230 can be coupled to the arm adapter 246.

Figure 2A:
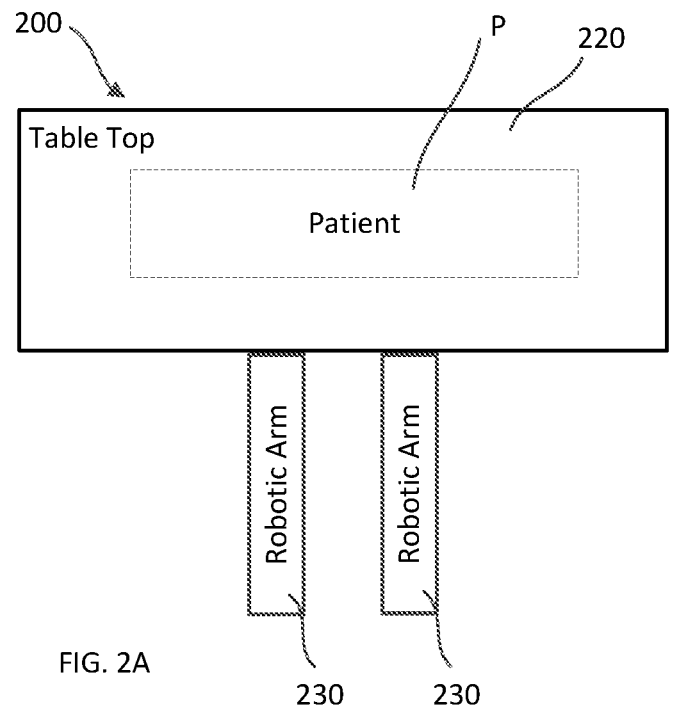
FIG. 2A is a schematic top view of a surgical table with robotic arms coupled thereto, according to an embodiment.
Figure 2B:
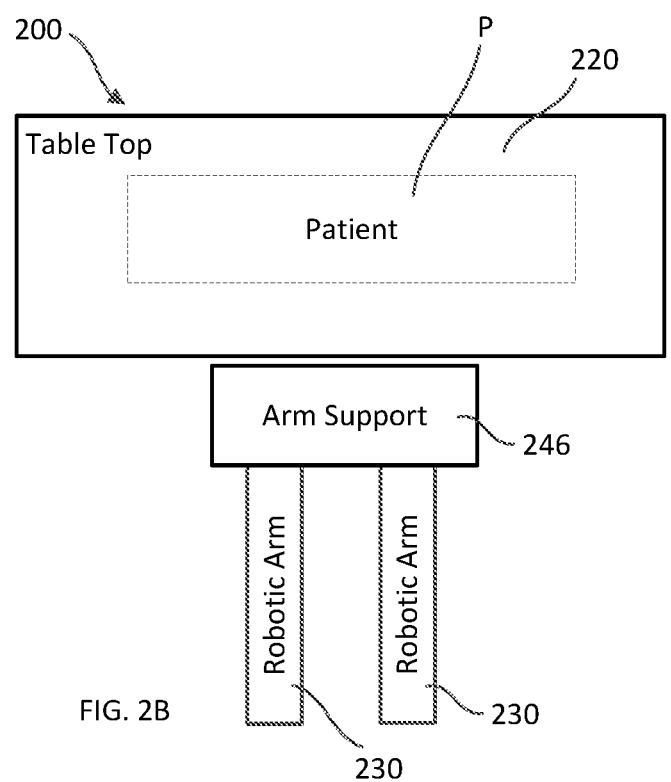
FIG. 2B is a schematic top view of a surgical table with robotic arms and an arm adapter coupled thereto, according to an embodiment.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. As shown schematically in FIG. 3, an arm cart 350 can be configured to support one or more robotic arms. The arm cart 350 includes a first robotic arm 330A and can include an optional second robotic arm 330B. Although two robotic arms 330A, 330B are shown, the arm cart 350 can be configured to contain, transport, and/or deliver any suitable number of robotic arms, such as, for example, one robotic arm, three robotic arms, or four robotic arms.

The arm cart 350 can support the first robotic arm 330A (and the optional second robotic arm 330B) in a variety of configurations. In some embodiments, the arm cart 350 can support the robotic arm 330A such that the center of gravity of the robotic arm 330A is below one or more support structure locations (e.g., cradles) of the arm cart 350 such that the stability of the robotic arm 330A and the arm cart 350 is increased. In some embodiments, the arm cart 350 can support the robotic arm 330A such that the arm cart 350 bears most or all of the weight of the robotic arm 330A and a coupling mechanism (not shown) of the robotic arm 330A can be manually manipulated by a user without the user bearing the most or all of the weight of the robotic arm. For example, the robotic arm 330A can be suspended from a structure of the arm cart 350 or rested on a structure of the arm cart 350. In some embodiments, the arm cart 350 can be configured to secure the robotic arm 330A to the arm cart 350.

The arm cart 350 can be configured for movement such as, for example, by including wheels. The arm cart 350 can be configured to protect the robotic arm 330A from potential impact with the surrounding of the arm cart 350 during, for example, transport or storage. In some embodiments, the arm cart 350 can be configured to move the robotic arm 330A between one or more positions and/or one or more orientations, including, for example, a folded storage or transport position and a deployed or coupling position.

The arm cart 350 can include an arm container 352 and a base 354. The arm container 352 is configured to support, protect, and promote sterility for one or more robotic arms (e.g., the first robotic arm 330A and the optional second robotic arm 330B) during transportation of the robotic arms, for example, from a storage area to the operating area, and during transfer of the one or more robotic arms from the arm cart 350 to a surgical table (e.g., the surgical table 100 and/or the surgical table 200) for use during the surgical procedure. While the one or more robotic arms 330A, 330B are stored and/or transported by the arm cart 350, the one or more robotic arms 330A, 330B can be mostly, substantially completely, or completely maintained within the footprint of the arm cart 350 such that the one or more robotic arms 330A, 330B will be less likely to be accidentally bumped or damaged. In some embodiments, the arm container 352 can be structured as a vertically-extending protection frame that, in combination with the base 354, defines a space for storing the one or more robotic arms 330A, 330B. In some embodiments, when the one or more robotic arms 330A, 330B are stored within the arm cart 350, the robotic arms 330A, 330B can be maintained within the perimeter of the base 354, but may extend beyond the perimeter of the arm container 352.

The arm container 352 can be further configured to facilitate safe, efficient, sterile, and repeatable transfer of the one or more robotic arms 330A, 330B to the surgical table and/or an arm adapter. In some embodiments, transfer of the one or more robotic arms 330A, 330B from the arm cart 350 to the surgical table can be performed manually.

The base 354 can be configured to support the arm container 352 and provide transportation of the arm cart 350 to the surgical area. The base 354 can include any suitable means for movement of the arm cart 350 relative to the floor. For example, the base 354 can include wheels such that a medical provider can push/pull the arm cart to/from the operating area.

The arm cart 350 can include features that assist in aligning the one or more robotic arms 330A, 330B for transfer to the surgical table along the X, Y, and/or Z axes and/or rotationally about the X, Y, and/or Z axes. For example, as described above, the base 354 can include any suitable means for movement of the arm cart 350 such that the arm cart 350 can be moved along the X axis and/or the Y axis relative to the surgical table. Additionally, the arm cart 350 can include any suitable means for adjusting the height of the arm cart 350 and/or the one or more robotic arms 330A, 330B such that the height of the one or more robotic arms 330A, 330B can be adjusted relative to the surgical table. Thus, the arm cart 350 can move the one or more robotic arms 330A, 330B along the X, Y, and/or Z axes and/or rotationally about the X, Y, and/or Z axes such that a coupling portion of at least one of the one or more robotic arms 330A, 330B can be aligned for engagement with a mating coupling portion on a table or a table adapter.

In some embodiments, the arm cart 350 houses the one or more robotic arms 330A, 330B such that a line of sight can be maintained from the operator of the arm cart 350 to the portion of the surgical table to which the one or more robotic arms 330A, 330B are to be transferred during the approach of the arm cart 350 to the surgical table and the transfer of the one or more robotic arms 330A, 330B to the surgical table.

Figure 3:
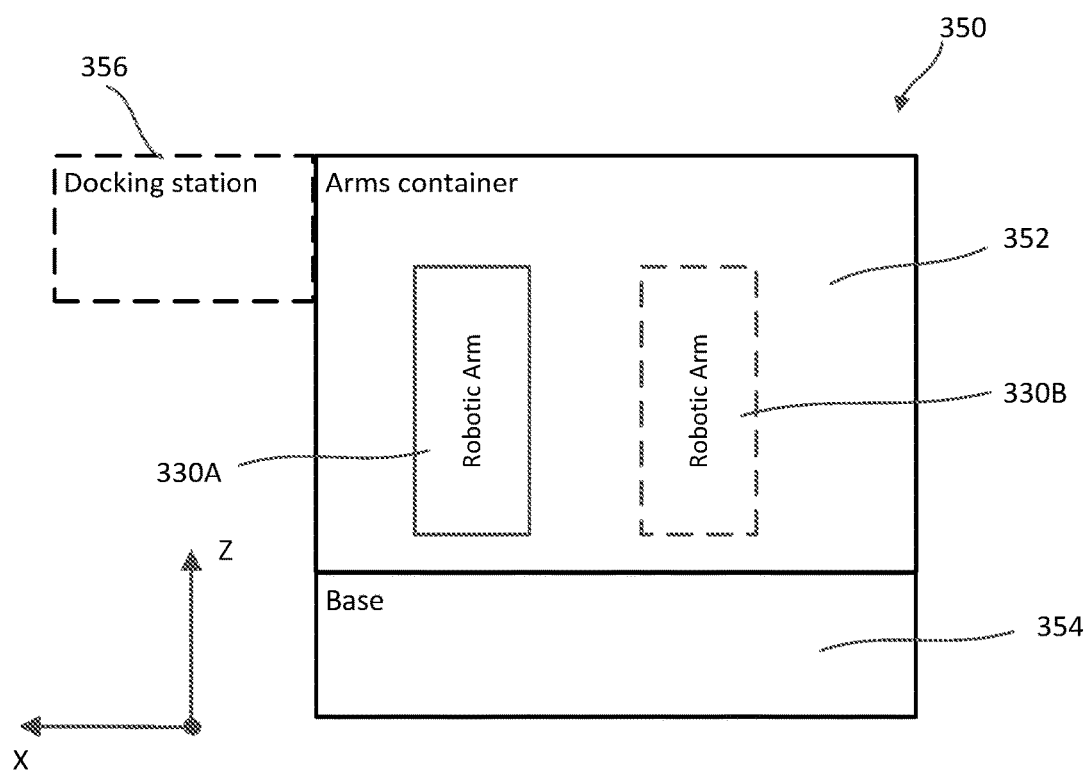
FIG. 3 is a schematic illustration of an arm cart according to an embodiment.

As shown in FIG. 3, the arm cart 350 may optionally include one or more docking stations 356 configured to be releasably attached to the surgical table and/or an arms support connected to the surgical table. In this manner, the arm cart 350 can be fixed to the surgical table and/or arms support during transfer of one or more robotic arms 330A, 330B from the arm cart 350, and then the arm cart 350 can be removed from the operating area.

The one or more robotic arms 330A, 330B can be docked and/or mounted to the surgical table using a variety of different types of coupling and/or mounting methods and mechanisms. The arm cart 350 can employ corresponding coupling methods and mechanisms to provide efficient transfer of the robotic arms 330A, 330B from the arm cart 350 to any suitable location on the surgical table and/or an arms support associated with the surgical table. In this manner, the arm cart 350 and the surgical table can include a common interface such that the robotic arms 330A, 330B can be efficiently and repeatedly coupled to and/or removed from the surgical table and the arm cart 350.

Figure 4:
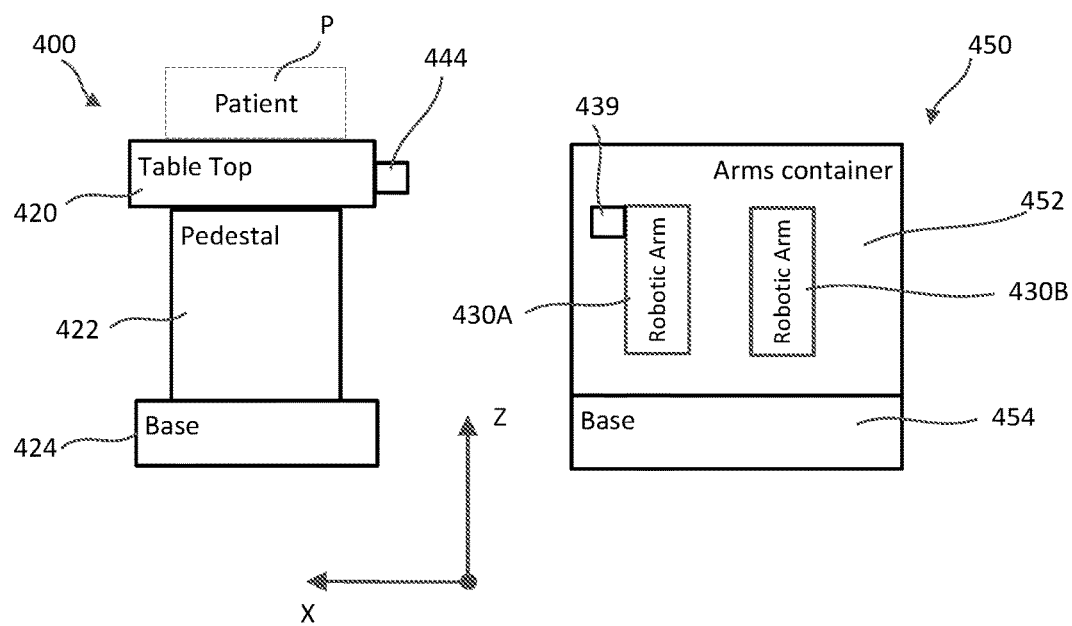
FIG. 4 is a schematic illustration of an arm cart and a surgical table, according to an embodiment.

In some embodiments, a first coupling member associated with the robotic arm can be configured to engage with a second coupling member (e.g., coupling site) associated with the surgical table. For example, FIG. 4 is a schematic illustration of an arm cart 450 and a surgical table 400. The arm cart 450 can be the same or similar in structure and/or function to any of the arm carts described herein (e.g., arm cart 350). For example, the arm cart 450 can include an arm container 452 and a base 454. The arm container 452 is configured to support, protect, and promote sterility for one or more robotic arms (e.g., a first robotic arm 430A and a second robotic arm 430B) during transportation of the robotic arms, for example, from a storage area to the operating area, and during transfer of the robotic arms from the arm cart 450 to the surgical table 400 for use during the surgical procedure. The arm container 452 is further configured to facilitate safe, efficient, sterile, and repeatable transfer of the surgical arms to the surgical table 400. Transfer of the robotic arms from the arm cart 450 to the surgical table 400 may be performed manually. The surgical table 400 can be the same or similar to any of the surgical tables described herein (e.g., the surgical table 100). For example, the surgical table 400 includes a table top 420, a support 422, and a base 424. A patient P can be disposed on the table top 420.

A first coupling member 439 is coupled to the robotic arm 430A. A second coupling member 1044 can be coupled to the table top 420 and/or the pedestal 422 of the surgical table 400. The first coupling member 439 and the second coupling member 444 (also referred to herein in combination as a "coupler") can include any suitable complementary releasable coupling means. In some embodiments, the arm cart 450 and/or the surgical table 400 can include alignment features to assist in achieving the proper alignment (e.g., along and/or about the X, Y, and/or Z axes) between the first coupling member 439 and/or the second coupling member 444.

Although the second coupling member 444 is shown as being disposed to the side of the table top 420, in some embodiments, the second coupling member can be disposed on the bottom or the top of the table top 420. Similarly, although the second coupling member 444 is shown and described as being coupled to the table top 420, in some embodiments the second coupling member 444 can be coupled to any suitable portion of the surgical table 400, such as, for example, the pedestal 422 or the base 424.

Figure 5:
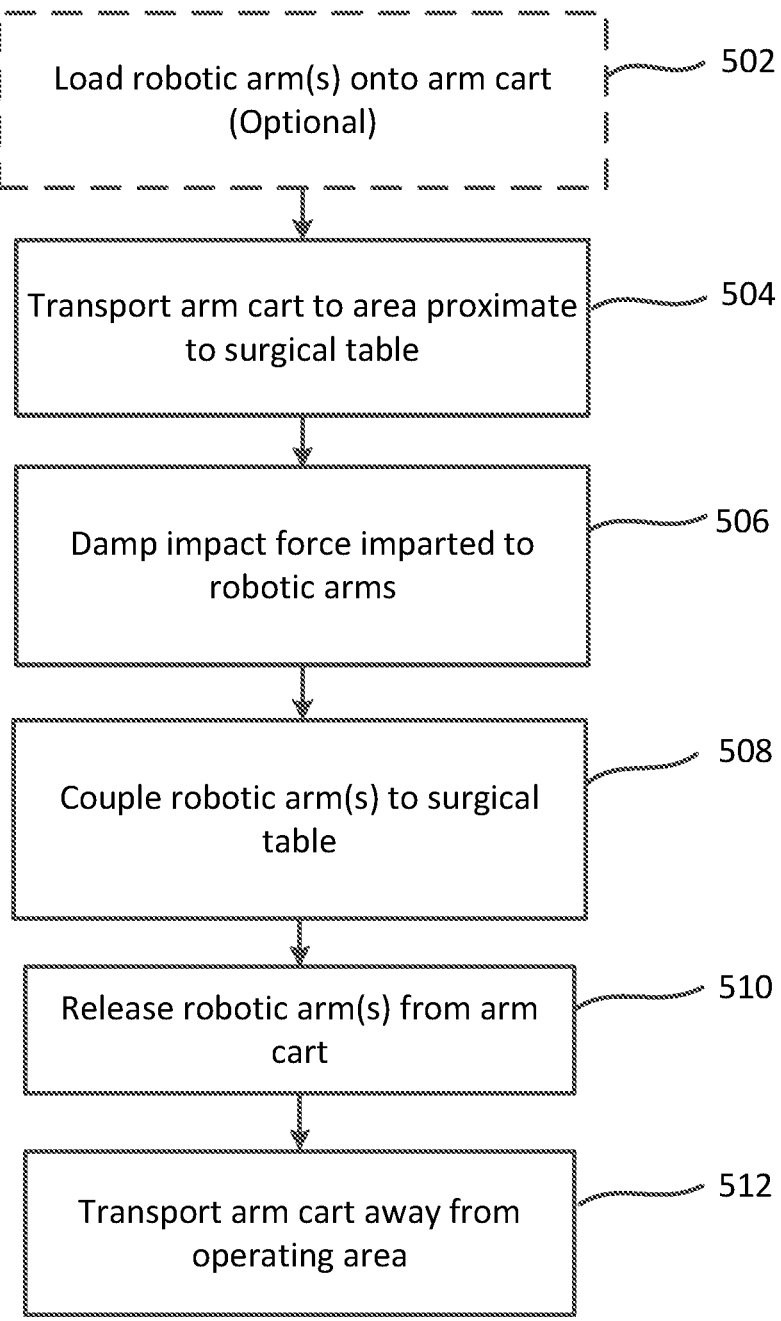
FIG. 5 is a flowchart of a method of using an arm cart to transfer robotic arms to a surgical table, according to an embodiment.

FIG. 5 is a flow chart of a method 500 of transporting and transferring surgical robotic arms to a surgical table using a surgical robotic arm cart, such as any of the arm carts described herein. The method 500 may optionally include loading one or more robotic arms onto an arm cart, at 502. For example, one or more robotic arms can be releasably coupled to an arm support of the arm cart. The arm support can be coupled to a base of the arm cart to support the one or more robotic arms above the base. In some embodiments, the arm cart may function as a storage container for the one or more robotic arms; therefore, the robotic arms may be preloaded within the arm cart and the step of loading the one or more robotic arms onto the arm cart may be omitted. The base can be freely movable on a support surface. At 504, the arm cart is transported to an operating area and adjacent to a surgical table.

The arm cart may damp or absorb impact or shock forces acting on the one or more robotic arms, at 506. For example, the arm cart may include damping mechanisms, as described herein, that may absorb shock forces when the arm cart or the one or more robotic arms comes into contact with an object, including, for example, the surgical table, a wall, equipment, a tool, etc. The arm cart may protect the one or more robotic arms from damage due to shock forces by damping or absorbing the shock forces. The damping mechanisms may be mechanical, electrical, magnetic, or some combination thereof. For example, the damping mechanisms can be a spring and a dashpot. The damping mechanisms can be disposed on or form a part of a base or an arm support of the arm cart. In some embodiments, the damping mechanisms can prevent damage to a robotic arm during attachment of the robotic arm to the surgical table. For example, a user may steer the arm cart toward a surgical table to engage a portion of a robotic arm, such as a couple of the robotic arm, with the surgical table. When the user engages the robotic arm with the surgical table at a high speed, the robotic arm may be subjected to an impact or shock force that can damage the arm. To prevent damage to the arm, the arm cart may be equipped with a damping mechanism that reduces the shock force.

In some embodiments, if not yet disposed in proper alignment with the surgical table, an arm portion of a coupler disposed on at least one of the one or more robotic arms can be disposed in operative relationship with a table portion of a coupler disposed on the surgical table. For example, the arm cart can move a robotic arm within the arm cart such that a coupling member associated with the robotic arm can be presented at a suitable location for engagement with a complementary coupling member associated with a table. The arm cart can adjust the robotic arm to various height settings such that the robotic arm can cooperate with various surgical tables and/or various coupling portions of a surgical table at varying heights. Once the robotic arm is aligned with the surgical table, the robotic arm can be coupled to the surgical table, at 508. For example, in some embodiments, the arm portion of the coupler can be releasably coupled to the table portion of the coupler. At 510, the robotic arm is released from the arm cart. At 512, the arm cart is transported away from the operating area.

In some embodiments, if a second robotic arm has been loaded onto the arm cart (or is stored in the arm cart), the arm cart can couple a first robotic arm to the surgical table, release the first robotic arm from the arm cart, and be transported to a location adjacent to another portion of the surgical table. If not yet disposed in proper alignment with the surgical table, an arm portion of a second coupler disposed on the second robotic arm can be disposed in operative relationship with a table portion of a second coupler disposed on the surgical table. The second robotic arm can then be coupled to the surgical table via, for example, the arm portion of the second coupler being releasably coupled to the table portion of the second coupler. The second robotic arm can be released from the arm cart and the arm cart can be transported away from the operating area.

Figure 6:
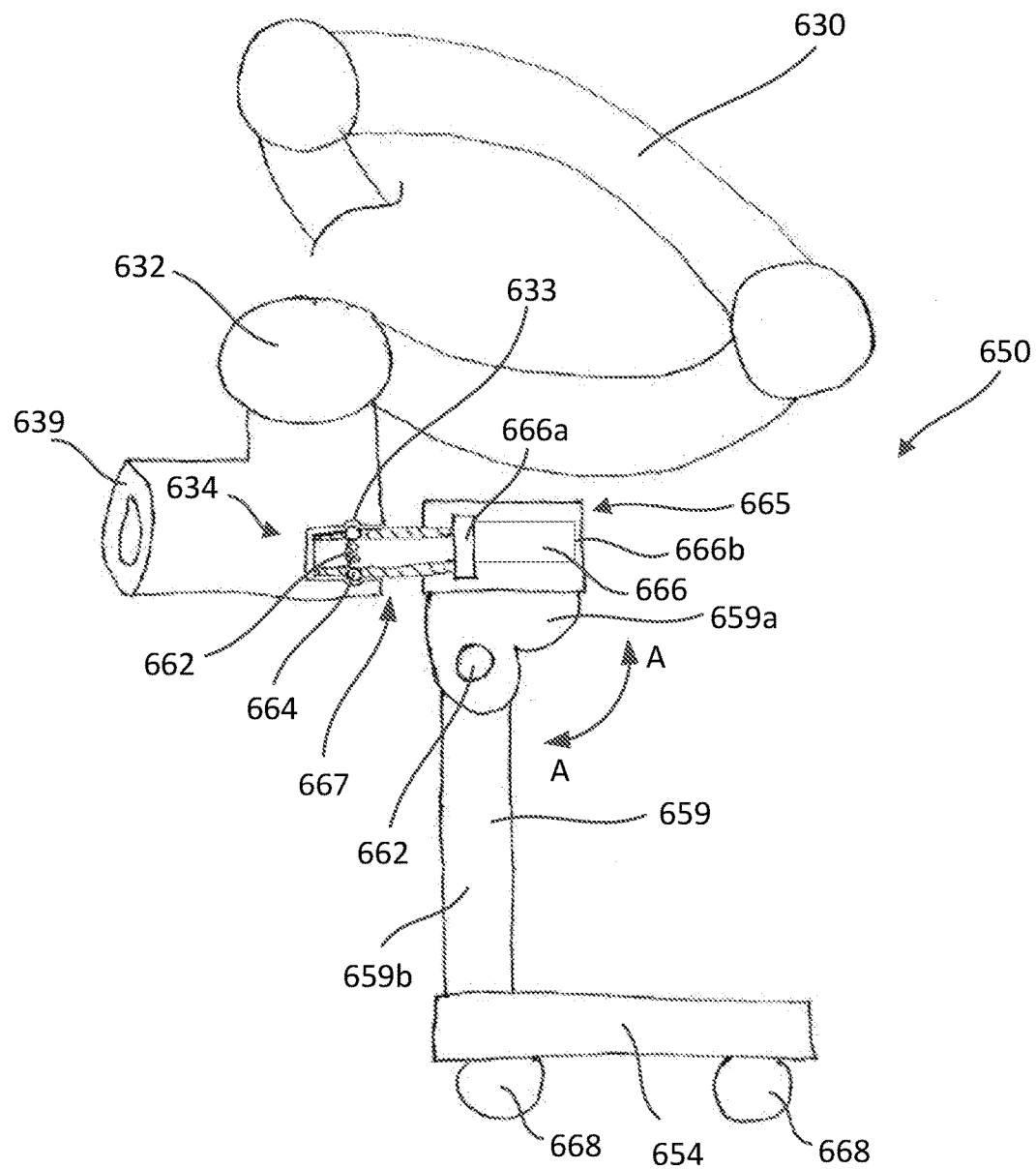
FIG. 6 is a schematic illustration of an arm cart having a damping mechanism, according to an embodiment.

FIG. 6 is a schematic illustration of an example arm cart 650 engaged with a robotic arm 630, according to an embodiment. The arm cart 650 may be similar in structure and/or function to any of the arm carts described herein. For example, the arm cart 650 can include an arm support 659 and a base 654. The base 654 can be freely moveable on a support surface, such as, for example, a floor, between a location remote from a surgical table and a location proximate to the surgical table. For example, the base 654 can be coupled to a number of wheels 668, such as, for example, three or four wheels, such that the arm cart 650 is moveably supported on the support surface.

The robotic arm 630 can be similar in structure and/or function to any of the robotic arms described herein. For example, the robotic arm 630 can include a target joint 632 and an arm coupling member 639 (also referred to as a "coupler"). The arm coupling member 639 can include an engagement feature 634 configured for engagement with a docking pin 667. The engagement feature 634 can be shaped, for example, as a cylindrical space with detents 633 having a shape complementary to balls 664 of the docking pin 667. In other embodiments, the engagement feature 634 may also be shaped as a rectangular prism and/or have one or more tapered surfaces.

The arm support 659 includes a first portion 659a and a second portion 659b. As depicted in FIG. 6, the arm support 659 can support the robotic arm 630 above the base 654. A docking assembly 665 can be coupled to the first portion 659a of the arm support 659. The first portion 659a of the arm support 659 can rotate relative to the second portion 659b of the arm support 659 about a pivot point 662. When the first portion 659a rotates relative to the second portion 659b, the docking assembly 665 rotates along an arrow A-A. The rotation of the first portion 659a of the arm support 659 can be assisted by mechanical means such as springs, shocks, pressure cylinders, and/or a motor. In a specific embodiment, the first portion 659a can rotate by an angle of 90°.

The docking assembly 665 includes an engagement feature such as the docking pin 667. The docking pin 667 can include a spring 662 and two or more balls 664. The balls 664 of the docking pin 667 can be configured to engage with a feature formed in a portion of the robotic arm 630, such as the coupling member 639. For example, the balls 664 can engage with the detents 633 having a shape complementary to the balls 664 of the docking pin 667. The detents 633 may be disposed in the engagement feature 634, as shown in FIG. 6. In use, the robotic arm 630 can be coupled to the arm cart 650 via the docking assembly 665. The docking pin 667 of the docking assembly 665 can be inserted into the recess in the coupling member 639 until the spring 663 pushes the balls 664 outwardly into releasable engagement with the detents 633 such that the robotic arm 630 and the arm cart 650 are in a coupled configuration, as shown in FIG. 6.

When the arm cart 650 and the robotic arm 630 are coupled together, the robotic arm 630 can be rotated between a stored position and a deployed position via the first portion 659a of the robotic arm 659 along arrow A-A. When the robotic arm 630 is in the stored position, the arm cart 650 can be moved from a location remote from the surgical table to a location proximate to the surgical table. The robotic arm 630 can then be rotated via the first portion 659a of the robotic arm 659 along arrow A-A to the deployed position in which a portion of the robotic arm 630 is exposed to contact the surgical table. For example, the coupling member 639 can be exposed such that it can engage with a coupling site of the surgical table. When the robotic arm 630 is in the deployed position, the arm cart 650 can be moved closer to the surgical table such that the exposed portion of the robotic arm 630 (e.g., the coupling member 639) contacts the surgical table.

To reduce the possibility of damage to the arm 630, cart 650, or surgical table due to the engagement of the arm 630 with the table, a damping mechanism 666 can be provided. The damping mechanism 666 can absorb shock experienced by the robotic arm 630 during or as a result of the coupling member 639 contacting and engaging with a coupling site of the surgical table. The robotic arm 630 may experience shock, for example, when the coupling member 639 of robotic arm 630 contacts the surgical table at a high velocity, such as when the arm cart 650 advances too quickly toward the surgical table. The damping mechanism 666 can absorb at least a portion of the force experienced by the coupling member 639 when the contact between the coupling member 639 and the surgical table occurs. The coupling member 639 can then be pushed into complete engagement with the surgical table.

In some embodiments, the damping mechanism 666 can include, for example, a mechanical damper such as a spring and/or a dashpot. In other embodiments, the damping mechanism 666 can be an electrical damper, a magnetic damper, or other type of mechanism capable of reducing or damping a force transferred or imparted to the robotic arm 630 due to its contact with another object, such as the surgical table. The damping mechanism 666 can have a first end 666a that is coupled to the docking pin 667 and a second end 666b that is coupled to a portion of the docking assembly 665. When a shock or impact force is transferred to the robotic arm 630 due to its contact with the surgical table, the first end 666a of the damping mechanism 666 may move toward the second end 666b of the damping mechanism 666 while exerting a damping force in an opposite direction to counteract the impact force. For example, the damping mechanism 666 can be a spring. When the robotic arm 630 contacts the surgical table and experiences a shock or impact force due to the contact, a first end of the spring (e.g., the first end 666a) can compress toward a second end of the spring (e.g., the second end 666b). When this compression occurs, the spring can exert a force back toward its equilibrium or resting position, which acts to reduce or damp the impact force. As another example, the damping mechanism 666 can be a dashpot with a piston disposed proximate to a first end (e.g., the first end 666a) of a cylinder that can displace toward a second end (e.g., the second end 666b) of the cylinder. The dashpot may have a gas or fluid (e.g., air, oil, etc.) that becomes pressurized as the piston moves towards the second end but can slowly flow out from the cylinder through one or more openings. The dashpot can exert a force in a direction opposite to the direction of movement of the piston that reduces or damps the impact force. By reducing the impact force, the damping mechanism 666 can control a rate at which the coupling member 639 engages with the coupling site of a surgical table (e.g., a rate at which the coupling member 639 slides into an opening formed in a coupling site of the surgical table).

After the coupling member 639 has been coupled to the surgical table, a pulling force can be applied to the arm cart 650 to separate the docking pin 667 from the coupling member 639. Since the docking pin 667 is coupled to the coupling member 639 via the balls 664, which are driven outwardly by the spring 662 into the detents 633, the docking pin 667 can separate from the coupling member 639 when the pulling force is sufficient to overcome the force of the spring 662 holding the balls 664 in the detents 633. The spring 662 may be designed to be easily overcome such that the docking pin 667 only maintains a "soft" hold on the coupling member 639. When the docking pin 667 is separated from the coupling member 639, the arm cart 650 can be moved away from the location proximate to the surgical table.

Although the arm cart 650 is described as storing, deploying, and transferring one robotic arm 630, in some embodiments the arm cart 650 can store, deploy, and transfer a second robotic arm similarly as described above with respect to the robotic arm 630. For example, both the robotic arm 630 and a second robotic arm can be loaded onto the arm cart 650 prior to transfer of either robotic arm to a surgical table. The arm cart 650 can include a second arm support and the second robotic arm can be loaded into engagement with the second arm support. After transferring the robotic arm 630 to a first coupling site of a surgical table as described above, the arm cart 650 can be moved, with the second robotic arm in a stowed configuration, via the base 654 to another location near the surgical table. The second arm support can then move the second robotic arm similarly as described above from the stowed configuration to the deployed configuration such that a coupler of the second robotic arm can be disposed in a proper position for engagement with a second coupling site associated with the surgical table. Once properly aligned with a coupling site of a surgical table, the second robotic arm can be transferred to the surgical table and the arm cart 650 can be moved away from the surgical table.

Figure 7A:
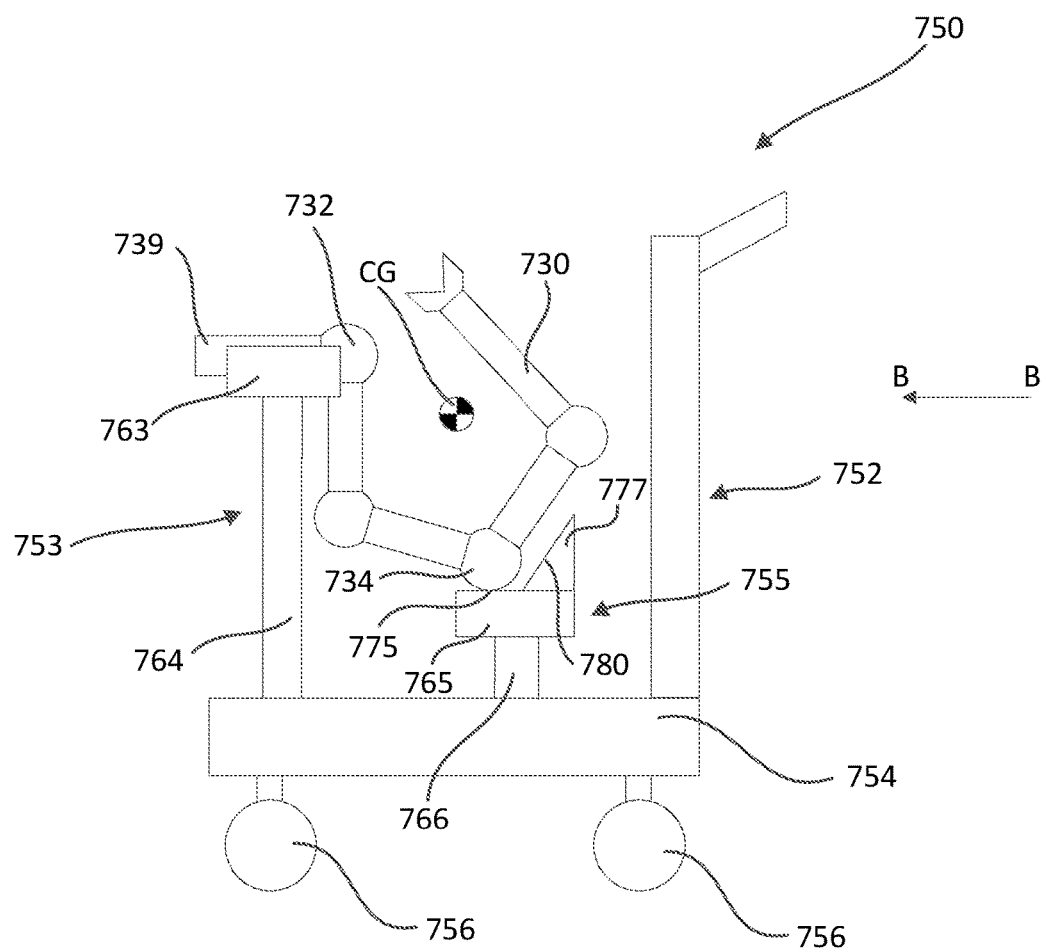
FIGS. 7A, 7B, and 7C are schematic illustrations of an arm cart having a damping mechanism that is capable of supporting a robotic arm such that a center of gravity of the robotic arm is below an arm support, according to an embodiment.
Figure 7B:
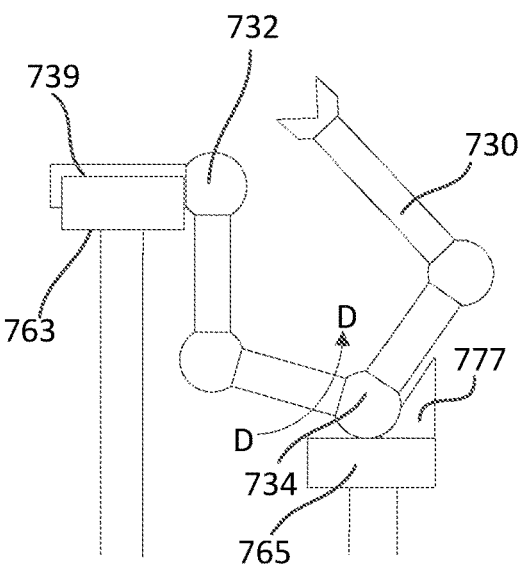
Figure 7C:
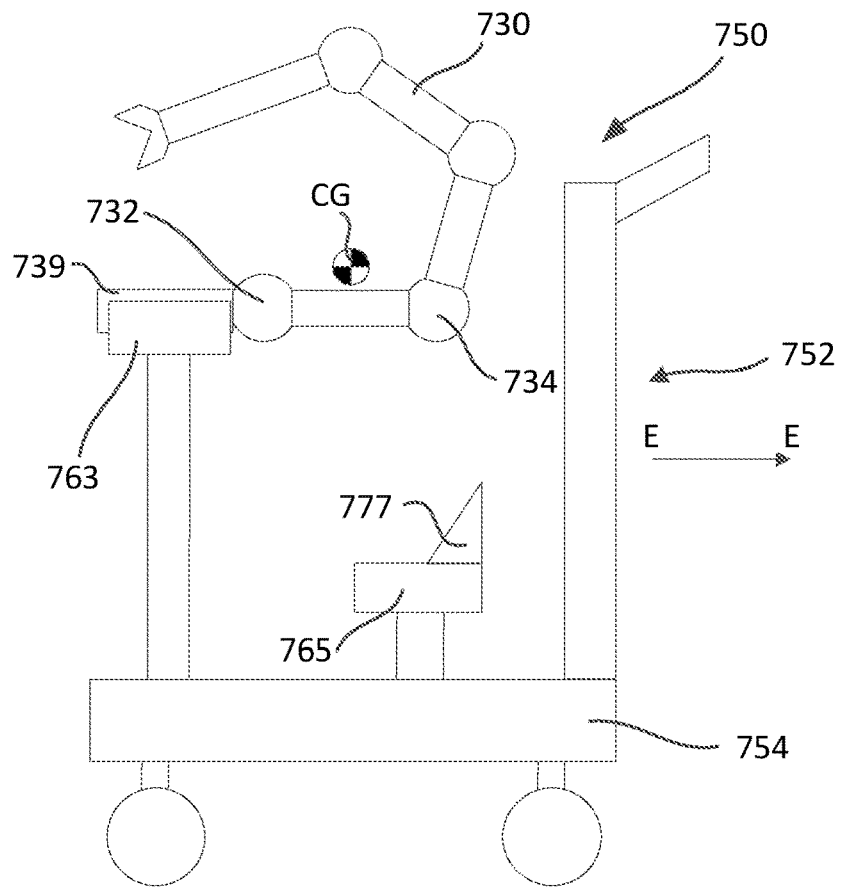

FIGS. 7A-7C depict an example arm cart 750 engaged with a robotic arm 730, according to an embodiment. The arm cart 750 can be similar in structure and/or function to any of the arm carts described herein. For example, the arm cart 750 includes an arm container 752 and a base 754. The arm container 752 can be coupled to and extend upwardly from the base 754. The base 754 can be freely moveable on a support surface, such as, for example, a floor, between a first location remote from a surgical table and a second location adjacent to the surgical table. For example, the base 754 can be coupled to a number of wheels 756, such as, for example, three or four wheels, such that the arm cart 750 is moveably supported on the support surface. The arm cart 750 can also include a first arm support 753 and a second arm support 755. The second arm support 755 can include a backstop 777.

The robotic arm 730 can be similar in structure and/or function to any of the robotic arms described herein. For example, the robotic arm 730 can include an arm coupling member 739 (also referred to as a "coupler") that is configured to couple to a coupling site of a surgical table. The robotic arm 730 can also include one or more joints 732, 734, which can allow the robotic arm to rotate or pivot in one or more directions. For example, the joint 732 may be disposed adjacent to the coupling member 739 and can provide a pivot point to allow a distal segment of the robotic arm 730 to pivot relative to the arm cart 750 and a surgical table.

The arm cart 750 is configured to support the robotic arm 730 such that a center of gravity CG of the robotic arm 730 is disposed below a portion of the first arm support 753 (e.g., a cradle 763 of the first arm support 753). As shown in FIG. 7A, the first arm support 753 and the second arm support 755 can be positioned on opposite sides of the center of gravity CG of the robotic arm 730 such that the bending moments needed to support the robotic arm 730 are minimized. The first arm support 753 may have a first support member 764 and a first cradle 763, and the second arm support 755 may have a second support member 766 and a cradle 765. The robotic arm 730 can be held in position on the two cradles 763, 765 by gravity. As depicted in FIG. 7A, the coupling member 739 can be held by the first cradle 763, and the joint 734 can be held by the second cradle 765. The two cradles 763, 765 can be stationary relative to the base 754 and no latch is needed to maintain the robotic arm 730 on the arm container 752. In some embodiments, substantially the entire robotic arm 730 except the coupling member 739 can be disposed within the arm container 752 and protected by the arm container 752 from impact with objects during movement of the arm cart 750 on the support surface. The arm container 752 can include one or more side walls (not depicted) that can protect the robotic arm 730 from side impacts.

The arm cart 750 can also include one or more features for damping a shock or impact force experienced by the arm cart 730 when the arm cart 730 comes into contact with another object. As depicted in FIG. 7A, the coupling member 739 of the arm cart 730 can be disposed outside of the arm container 752 and, therefore, is not protected by the arm container 752 and may come into contact with other objects. When one or more robotic arms are loaded onto the arm cart 750, the arm cart 750 may be heavy and therefore difficult to steer and/or slow down due to its high momentum. Thus, while transporting the arm cart 750 to a location proximate to the surgical table, and while engaging the robotic arm 730 with a portion of the surgical table, the robotic arm 730 may contact the surgical table or other objects, including walls, equipment, tools, etc., at a high velocity that can damage the robotic arm 730, the surgical table, or other objects. Accordingly, the arm cart 750 may be equipped with one or more damping features to reduce the possibility of damage to the arm 730, the surgical table, or other objects.

For example, the backstop 777 of the arm cart 750 can act to damp shock or impact forces experienced by the coupling member 739. The backstop 777 can have an inclined surface 780 that is configured to reduce an impact force. As depicted in FIG. 7A, the backstop 777 is disposed on a surface 775 of the second arm support 765. A portion of the robotic arm 730 (e.g., the joint 734) can be supported on the surface 775. When the coupling member 739 of the robotic arm 730 contacts another object (e.g., the surgical table), the contact between the robotic arm 730 and the object can generate a force that causes the robotic arm 730 to move or slide toward the backstop 777 until the portion of the robotic arm 730 supported on the surface 775 engages with the inclined surface 780, as shown in FIG. 7B. Once the portion of the robotic arm 730 engages with the inclined surface 780, the inclined surface 780 can reduce the impact force by directing the movement of the backstop 777 upward such that gravity (in addition to any frictional forces between the robotic arm 730 and the inclined surface 780 or other surfaces of the arm cart 750) can act to reduce the force experienced by the robotic arm 730. In some embodiments, the backstop 777 can be formed of a shock-absorbing material, such as a flexible or soft polymer, that can compress to absorb or reduce a shock force experienced by the robotic arm 730. In some embodiments, a shock-absorbing material or a damper (e.g., a spring) can be disposed on the inclined surface 780 to absorb shock from the robotic arm 730.

In use, as shown in FIGS. 7A-7C, the robotic arm 730 can be loaded onto the arm cart 750. The robotic arm 730 can be positioned within the arm cart 750 such that the center of gravity CG of the robotic arm 730 is disposed below the first cradle 763, as shown in FIG. 7A. The arm cart 750 can be moved to a location proximate to the surgical table in which the coupling member 739 of the robotic arm 730 contacts a portion of the surgical table. The backstop 777 can reduce any impact forces imparted to the robotic arm 730 by the surgical table due to the contact between the coupling member 739 and the surgical table. For example, as described above, the backstop 777 can have an inclined surface 780 that reduces impact forces imparted to the robotic arm 730. The backstop 777 can also be made of a shock-absorbing, compressible material that reduces impact forces imparted to the robotic arm 730. The coupling member 739 can be aligned with a coupling site of the surgical table and be coupled to the surgical table. After the coupling member 739 is coupled to the surgical table, the robotic arm 730 can be pivoted along an arrow D-D, as shown in FIG. 7B, such that the robotic arm 730 is moved up and out of the second cradle 765. In some embodiments, power can be provided from the surgical table to the robotic arm 730 via the coupler 739. The surgical arm 730 can include at least one joint, such as the joint 732, separating a first portion of the robotic arm 730 (e.g., the portion including coupler 739) from a second portion of the robotic arm 730. The joint 732 can enable movement of the first portion of the robotic arm 730 relative to the second portion of the arm 730 using the power provided by the surgical table. For example, after coupling the coupler 739 of the robotic arm 730 to a coupling site or coupler associated with the surgical table, the second portion of the robotic arm 730 can be caused to move about the joint 732 such that the second portion of the robotic arm 730 is moved away from the second arm support 755. In some embodiments, the power provided from the surgical table to the robotic arm 730 can cause two or more portions of the robotic arm 730 to rotate relative to two or more joints of the robotic arm 730 away from the arm cart 750. As shown in FIG. 7C, when the robotic arm 730 has pivoted high enough (e.g., to a position in which the center of gravity CG of the arm is disposed above the first cradle 763) and the robotic arm 730 does not obstruct movement of the arm cart 750, the arm cart 750 can be moved away or separated from the robotic arm 730, such as along arrow E-E.

In some embodiments, the robotic arm 730 can be manually pivoted about the joint 732 to move the robotic arm 730 from the position shown in FIGS. 7A and 7B to the position shown in FIG. 7C. In some embodiments, the robotic arm 730 may also include a battery pack or other portable power source that can be used to power the robotic arm 730 and pivot the arm 730 about the joint 732. In such embodiments, the robotic arm 730 can include a switch or some other type of control component that can be manipulated by a user to pivot the robotic arm 730 about the joint 732. Alternatively, a user may communicate instructions to the robotic arm 730 either via a wired or wireless connection to cause the robotic arm 730 to pivot about the joint 732 out of the arm container 752.

Although the arm cart 750 is described as storing, deploying, and transferring one robotic arm 730, in some embodiments the arm cart 750 can store, deploy, and transfer a second robotic arm similarly as described above with respect to the robotic arm 730. For example, both the robotic arm 730 and a second robotic arm can be loaded onto the arm cart 750 prior to transfer of either robotic arm to a surgical table. The arm cart 750 can include additional arm supports, similar to the arm supports 753, 755, and the second robotic arm can be loaded into engagement with the additional arm supports. In some embodiments, the arm supports 753, 755 can also be configured to support the second robotic arm in addition to the first robotic arm 730. After transferring the robotic arm 730 to a first coupling site of a surgical table as described above, the arm cart 750 can be moved, with the second robotic arm, via the base 754 to another location near the surgical table. The second robotic arm can then be coupled and transferred to the surgical table and the arm cart 750 can be moved away from the surgical table.

Figure 8A:
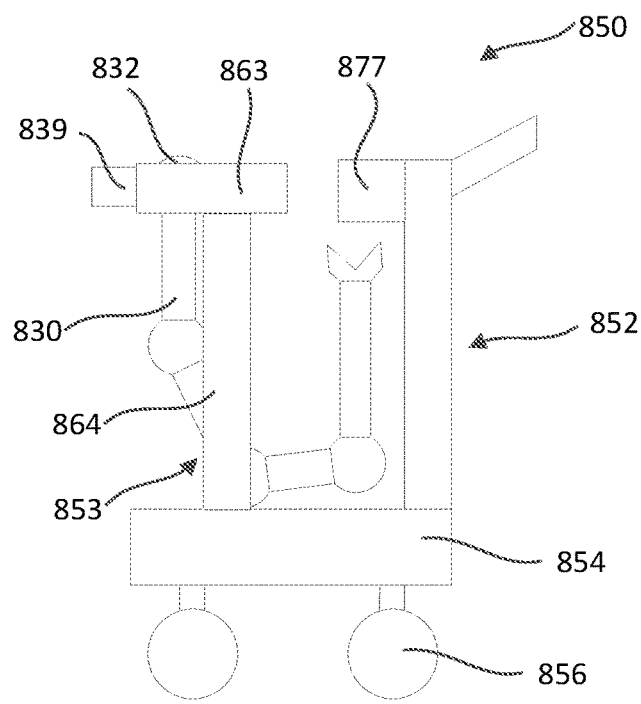
FIGS. 8A and 8B are schematic illustrations of an arm cart having a compliant or bendable arm support in different configurations, according to an embodiment.
Figure 8B:
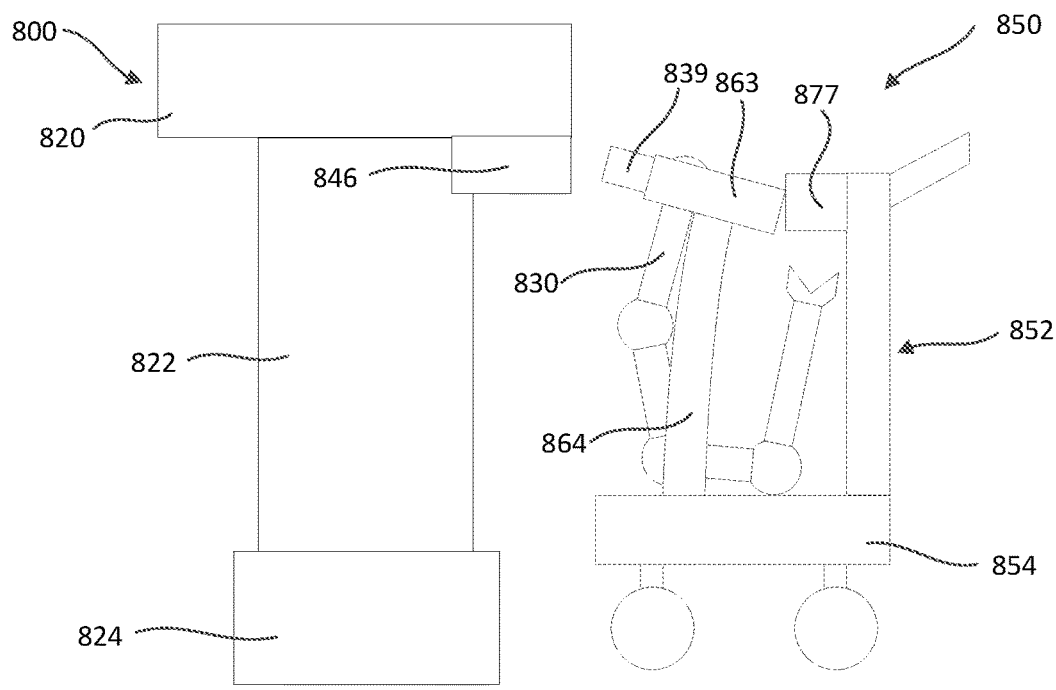

FIGS. 8A and 8B are schematic illustrations of another example arm cart 850 with a damping mechanism such as a flexible or complaint arm support 853. The arm cart 850 can be the same or similar in structure and/or function to any of the arm carts described herein. For example, the arm cart 850 includes an arm container 852 and a base 854. The arm container 852 can be coupled to and extend upwardly from the base 854. The base 854 can be freely moveable on a support surface, such as, for example, a floor, between a first location remote from a surgical table 800 and a second location adjacent to the surgical table 800 (as shown in FIG. 8B). For example, the base 854 can be coupled to a number of wheels 856, such as, for example, three or four wheels, such that the arm cart 850 is moveably supported on the support surface. The arm cart 850 can also include an arm support 853. The arm support 853 can include an arm cradle 863 and a post 864. The arm container 850 can optionally include a backstop 877.

The robotic arm 830 can be similar in structure and/or function to any of the robotic arms described herein. For example, the robotic arm 830 can include an arm coupling member 839 (also referred to as a "coupler"). The arm cart 850 is configured to support the robotic arm 830 such that the robotic arm 830 can be held in position on the arm cradle 863 by gravity. In some embodiments, the robotic arm 830 can include a cradle engagement feature, such as a protrusion (e.g., the docking pin 667), a latch, a hook, a recess, or other mechanism for coupling the robotic arm to the cradle 863. The cradle engagement feature can extend from a portion of the robotic arm 830 such as, for example, the joint 832. The cradle engagement feature can be disposed such that it can engage with the arm cradle 863 of the arm support 853. In some embodiments, the joint 832 can directly engage with the arm cradle 863 such that the arm cradle 863 supports the robotic arm 830 via the joint 832. The arm cradle 863 can be coupled to the arm post 864, and the arm post 864 can be coupled to the base 854. The robotic arm 730 can be supported by the arm support 853 such that no latch or other mechanism is needed to maintain the robotic arm 830 on the arm cart 750 when the arm cart 750 is being transported. In some embodiments, substantially the entire robotic arm 830 except the arm coupling member 839 can be disposed within the arm container 852 and protected by the arm container 852 from impact with objects during movement of the arm cart 850 on the support surface. The arm container 852 may have, for example, one or more side walls (not depicted) that can surround the robotic arm 830 and protect it from side impacts.

The surgical table 800, as depicted in FIG. 8B, can be similar in structure and/or function to any of the surgical tables described herein. For example, the surgical table 800 may have a table top 820, a support or pedestal 822, and a base 824. The support 822 can support the table top 820 at a suitable height above the floor. The surgical table 800 can also include a coupling member or coupling site 846 that can couple with the coupling member 839 of the robotic arm 830. Although the coupling site 846 is shown as being disposed below the table top 820, in some embodiments, the coupling site 846 can be disposed to the side or on the top of the table top 820.

The arm support 853 of the arm cart 850 may be structured similar to a cantilever such that it can provide compliance in one or two degrees of freedom. The post 864 of the arm support 853 can be configured to bend or flex in response to a shock or impact force applied to a portion of the robotic arm 830 (e.g., the coupling member 839). The post 864 can be formed of a material having a low elastic modulus but high tensile strength, including, for example, aluminum, titanium, acrylonitrile butadiene styrene (ABS), and polyoxymethylene such as DuPont™ Delrin®. The post 864 may provide structural rigidity and strength in a vertical direction (e.g., along a longitudinal length of the post 864) but be sufficiently compliant or flexible in a horizontal plane (e.g., along a lateral length of the post 864). The post 864 can be configured to bend to reduce an impact force imparted to the robotic arm 830 when the robotic arm 830 comes into contact with other objects, such as, for example, the surgical table 800, as depicted in FIG. 8B. When one or more robotic arms are loaded onto the arm cart 850, the arm cart 850 may be heavy and therefore difficult to steer and/or slow down due to its high momentum. Thus, while transporting the arm cart 850 to a location proximate to the surgical table, and while engaging the robotic arm 830 with a portion of the surgical table 800, the robotic arm 830 may contact the surgical table 800 or other objects, including walls, equipment, tools, etc., at a high velocity that can damage the robotic arm 830, the surgical table 800, or other objects. Accordingly, a compliant arm support, such as the arm support 853, may be provided to reduce the possibility of damage to the arm 830, the surgical table 800, and other objects.

In use, as shown in FIGS. 8A and 8B, the robotic arm 830 can be loaded onto the arm cart 850. The arm support 853 of the arm cart 850 can support the robotic arm 830 such that the coupling member 839 of the robotic arm 830 is exposed to contact a portion of the surgical table 800 (e.g., the coupling site 846 of the surgical table 800). The arm cart 850 can be moved from a location remote from the surgical table 800 to a location proximate to the surgical table 800. When the arm cart 850 is moved to the location proximate to the surgical table 800, the arm cart 850 may cause the coupling member 839 of the robotic arm 830 to contact a portion of the surgical table 800 (e.g., the coupling site 846 or some other structure of the surgical table 800). For illustration purposes, in FIG. 8B, the coupling member 839 is shown after having contacted the surgical table 800 with a momentum and velocity that generated an impact force with sufficient magnitude to have caused the post 864 of the arm support 853 to bend. By bending, the post 864 can absorb or reduce a portion of the impact force imparted to the robotic arm 830. The movement of the post 864 (and the corresponding movement of the cradle 863) allows the robotic arm 830 to translate and rotate relative to the base 854 of the arm cart 850. In some embodiments, the movement of the post 864 may be limited by a backstop 877, as shown in FIG. 8B. The backstop 877 can prevent the post 864 from bending beyond a certain point to avoid potential damage to other parts of the robotic arm 830 and/or the arm cart 850. For example, the backstop 877 can prevent the post 864 from bending too far back such that a lower portion of the arm 830 does not collide with the base 854 of the arm cart 850. After bending to damp the impact force, the post 864 can bend back to its original position, and the coupling member 839 of the robotic arm 830 can be coupled to the surgical table 800. In some embodiments, if the robotic arm 830 is not yet disposed in proper alignment with the surgical table 800, the arm cart 850 can be moved to align the robotic arm 830 with the surgical table 800 such that the two can be coupled together. The robotic arm 830 can then be decoupled or disengaged from the arm cart 850, and the arm cart 850 can be moved away from the surgical table 800 and the robotic arm 830.

Although the arm cart 850 is described as storing, deploying, and transferring one robotic arm 830, in some embodiments the arm cart 850 can store, deploy, and transfer a second robotic arm similarly as described above with respect to the robotic arm 830. For example, both the robotic arm 830 and a second robotic arm can be loaded onto the arm cart 850 prior to transfer of either robotic arm to a surgical table.

The arm cart 850 can include a second arm support, similar to the arm support 853, and the second robotic arm can be loaded into engagement with the second arm support. After transferring the robotic arm 830 to a first coupling site of a surgical table as described above, the arm cart 850 can be moved, with the second robotic arm, via the base 854 to another location near the surgical table. The second robotic arm can then be coupled and transferred to the surgical table and the arm cart 850 can be moved away from the surgical table.

Figure 9:
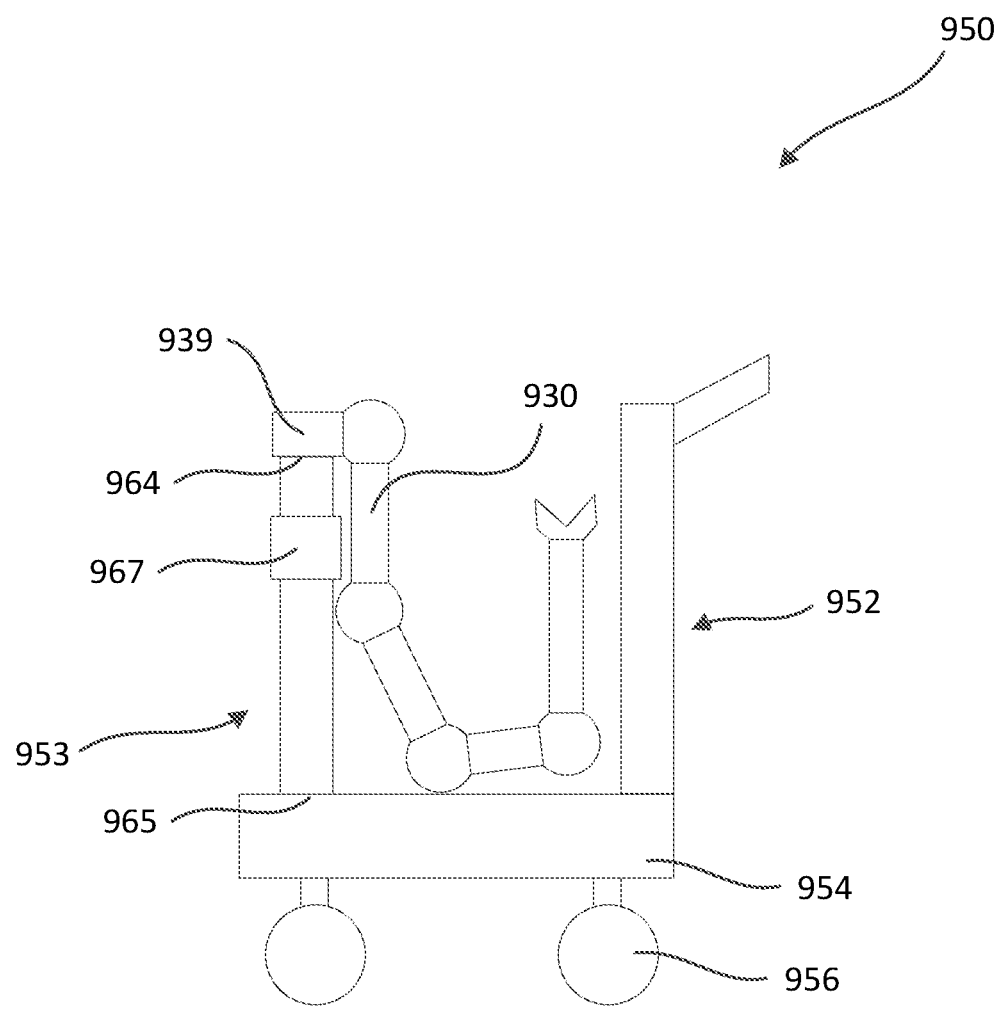
FIG. 9 is a schematic illustration of an arm cart having an arm support with a bendable joint, according to an embodiment.

In some embodiments, an arm cart can also have an arm support with a joint that enables it to bend and/or translate along one or more axes. For example, as depicted in FIG. 9, an arm cart 950 can have an arm support 953 that includes a joint 967. The arm cart 950 can be similar in structure and/or function to any of the arm carts described herein. For example, the arm cart 950 includes an arm container 952 and a base 954. The arm container 952 can be coupled to and extend upwardly from the base 954. The base 954 can be freely moveable on a support surface, such as, for example, a floor, between a first location remote from a surgical table and a second location adjacent to the surgical table. For example, the base 954 can be coupled to a number of wheels 956, such as, for example, three or four wheels, such that the arm cart 950 is moveably supported on the support surface. The arm cart 950 can also include an arm support 953.

The robotic arm 930 can be similar in structure and/or function to any of the robotic arms described herein. For example, the robotic arm 930 can include an arm coupling member 939 (also referred to as a "coupler"). The arm support 953 is configured to support the robotic arm 930 such that the arm coupling member 939 can contact and engage with a coupling site of a surgical table. The arm support 953 may be releasably coupled to the robotic arm 930. For example, one of the arm support 953 and the robotic arm 930 can include an engagement feature that is configured to releasably engage with a corresponding feature disposed on the other of the arm support 953 and the robotic arm 930. In some embodiments, the engagement feature can extend from a portion of the robotic arm 930 such as, for example, the coupling member 939. The engagement feature can be disposed such that it can engage with an end 964 of the arm support 953, as shown in FIG. 9. For example, the engagement feature can be disposed on a bottom side of the coupling member 939. The robotic arm 930 can be supported by the arm support 953 such that no latch or other mechanism is needed to maintain the robotic arm 930 on the arm cart 950 when the arm cart 950 is being transported. In some embodiments, substantially the entire robotic arm 930 except the arm coupling member 939 can be disposed within the arm container 952 and protected by the arm container 952 from impact with objects during movement of the arm cart 950 on the support surface. The arm container 952 may have, for example, one or more side walls (not depicted) that can surround the robotic arm 930 and protect it from side impacts.

As depicted in FIG. 9, the arm support 953 can be coupled to the base 954 at an end 965 and releasably coupled to the robotic arm 930 at the end 964. The arm support 953 can include a joint 967 that is configured to permit translation and rotation of the robotic arm 930 about at least one axis. For example, the joint 967 can include a flexible bellows that can rotate or bend in one or more directions. In some embodiments, the joint 967 can also be configured to translate in one or more directions. For example, the joint 967 can include a linear or curved track that allows a portion of the arm support 953 disposed above the joint 967 to translate along the track relative to a portion of the arm support 953 disposed below the joint 967. Similar to the arm support 853, the arm support 953 can be configured to bend to reduce an impact force imparted to the robotic arm 930 when the robotic arm 930 comes into contact with other objects, such as, for example, a surgical table.

In use, the robotic arm 930 can be loaded onto the arm cart 950. The arm support 953 of the arm cart 950 can support the robotic arm 930 such that the coupling member 939 of the robotic arm 930 is exposed for contacting a portion of a surgical table 800. The arm cart 950 can be moved from a location remote from the surgical table to a location proximate to the surgical table. When the arm cart 950 is moved to the location proximate to the surgical table, the arm cart 950 may cause the coupling member 939 of the robotic arm 930 to contact a portion of the surgical table. As a result of the contact, the robotic arm 930 may experience impact forces, which can cause the arm support 953 to bend or translate. By bending or translating, the arm support 953 can damp the impact forces. The arm support 953 can then return back or be returned back to its original position. For example, the arm support 953 can be biased to return back to its original position, or a user can manually move a portion of the arm support 953 that has moved due to the impact force back to its original position. In some embodiments, the arm cart 950 can also be electrically powered, and a user can manipulate one or more controls on the arm cart 950 to move the arm support 953 back to its original position. The coupling member 939 of the robotic arm 930 can then be aligned with and coupled to the surgical table, and the arm cart 950 can be decoupled and moved away from the robotic arm 930.

Although the arm cart 950 is described as storing, deploying, and transferring one robotic arm 930, in some embodiments the arm cart 950 can store, deploy, and transfer a second robotic arm similarly as described above with respect to the robotic arm 830. For example, both the robotic arm 930 and a second robotic arm can be loaded onto the arm cart 950 prior to transfer of either robotic arm to a surgical table. The arm cart 950 can include a second arm support, similar to the arm support 953, and the second robotic arm can be loaded into engagement with the second arm support. After transferring the robotic arm 930 to a first coupling site of a surgical table as described above, the arm cart 950 can be moved, with the second robotic arm, via the base 954 to another location near the surgical table. The second robotic arm can then be coupled and transferred to the surgical table and the arm cart 950 can be moved away from the surgical table.

Figure 10A:
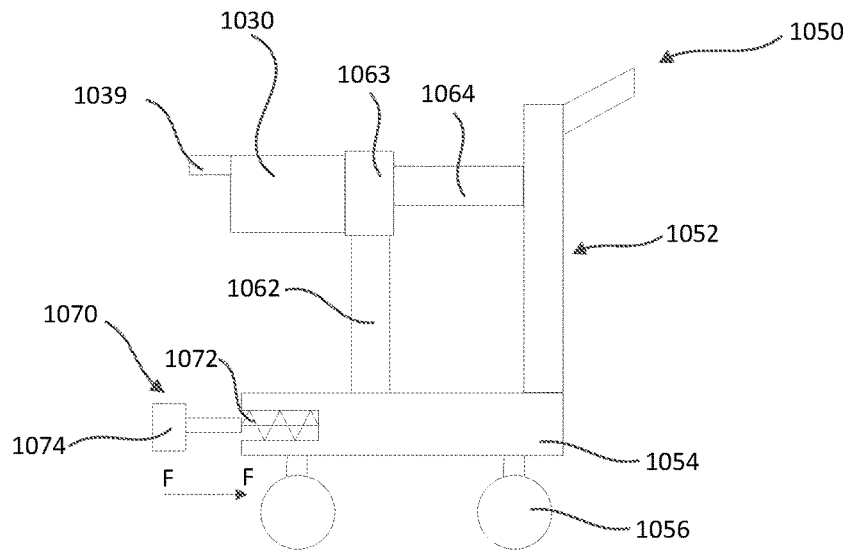
FIGS. 10A and 10B are schematic illustrations of an arm cart having a damping mechanism extending from a base of the cart in different configurations, according to an embodiment.
Figure 10B:
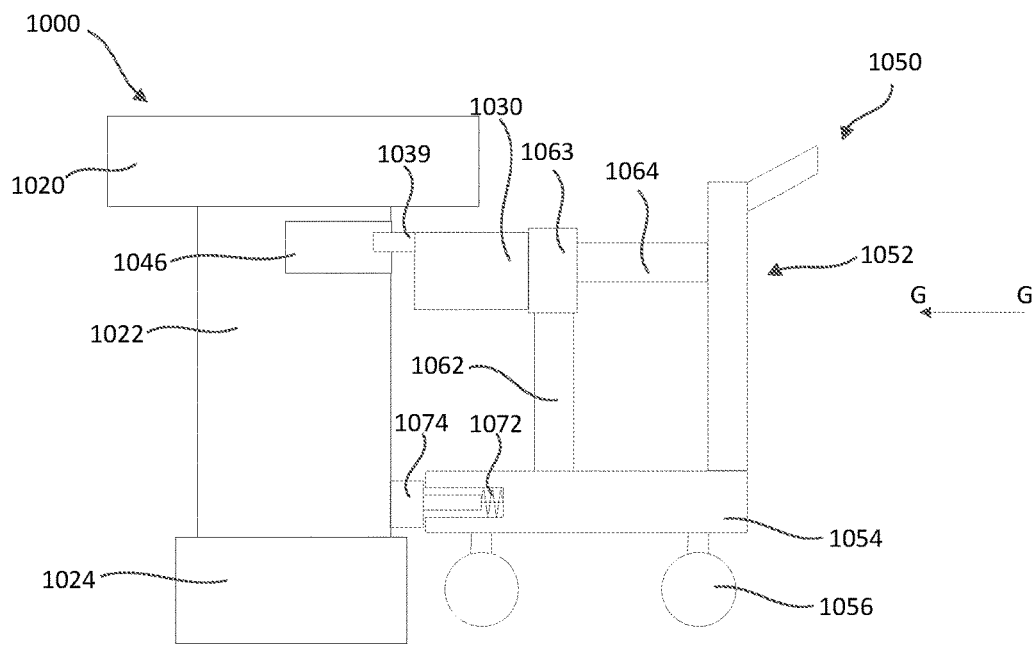

FIGS. 10A and 10B depict another example arm cart 1050 engaged with a robotic arm 1030, where the arm cart 1050 includes a damping mechanism 1070 that extends from a base 1054 of the arm cart 1050. The arm cart 1050 can be similar in structure and/or function to any of the arm carts described herein. For example, the arm cart 1050 includes an arm container 1052 and a base 1054. The arm container 1052 can be coupled to and extend upwardly from the base 1054. The base 1054 can be freely moveable on a support surface, such as, for example, a floor, between a first location remote from a surgical table 1000 and a second location adjacent to the surgical table 1000. For example, the base 1054 can be coupled to a number of wheels 1056, such as, for example, three or four wheels, such that the arm cart 1050 is moveably supported on the support surface.

The robotic arm 1030 can be similar in structure and/or function to any of the robotic arms described herein. For example, the robotic arm 1030 can include an arm coupling member 1039 (also referred to as a "coupler") that is configured to couple to a coupling site 1046 of the surgical table 1000. For schematic purposes, the robotic arm 1030 is shown generally in block form but, similar to other robotic arms described herein, can include one or more joints that can allow one or more segments of the robotic arm to move or rotate.

The arm cart 1050 can include multiple structures for supporting the robotic arm 1030. For example, as shown in FIG. 10A, the arm cart 1050 can include an arm support 1062 that is coupled to and extends from the base 1054. The arm support 1062 can have an attachment site 1063 (or cradle) that is configured to releasably couple to the robotic arm 1030. The arm cart 1050 can also have one or more additional structures, such as a post or beam 1064, that can attach to a portion of the arm support 1062 and support the arm support 1062, or can attach to other portions of the robotic arm 1030.

The arm cart 1050 also includes a damping mechanism 1070. The damping mechanism 1070 may be operatively coupled to the base 1054 such that it is movable between an extended position, as shown in FIG. 10A, and a retracted position, as shown in FIG. 10B. In the extended position, the damping mechanism 1070 extends from the base 1054 beyond the coupling member 1039 such that the damping mechanism 1070 prevents the coupling member 1039 from coupling to the coupling site 1046 of the surgical table 1000. As depicted in FIG. 10A, when the damping mechanism 1070 is in the extended position, the damping mechanism 1070 is configured to contact the surgical table 1000 before the coupling member 1039 can contact the coupling site 1046. When pressed against the surgical table 1000, the damping mechanism 1070 may retract along an arrow F-F to the retracted position, as shown in FIG. 10B. In the retracted position, the damping mechanism 1070 allows the coupling member 1039 to couple to the coupling site 1046. The damping mechanism 1070 can include a bumper 1074 that is mounted to a mechanical damper 1072 (also referred to as an "energy-absorbing component"). The mechanical damper 1072 can be, for example, a spring, a dashpot, or a combination thereof. In other embodiments, the damping mechanism 1070 can have an electrical damper, a magnetic damper, or other type of mechanism capable of damping a force. The bumper 1074 can have a low height (e.g., have a small lateral profile). In alternative embodiments, the bumper 1074 can be replaced by a larger protective cage that can extend a partial or full height of the arm cart 1050.

The surgical table 1000, as depicted in FIG. 10B, can be similar in structure and/or function to any of the surgical tables described herein. For example, the surgical table 1000 may have a table top 1020, a support or pedestal 1022, and a base 1024. The support 1022 can support the table top 1020 at a suitable height above the floor. The surgical table 1000 can also include a coupling member or coupling site 1046 that can couple with the coupling member 1039 of the robotic arm 1030. Although the coupling site 1046 is shown as being disposed below the table top 1020, in some embodiments, the coupling site 1046 can be disposed to the side or on the top of the table top 1020.

In use, the robotic arm 1030 can be loaded onto the arm cart 1050. The arm cart 1050 can be moved from a location remote from the surgical table 1000 to a location proximate to the surgical table 1000. When the arm cart 1050 is moved to the location proximate to the surgical table 1000, the bumper 1074 of the damping mechanism 1070 may contact a portion of the surgical table 1000 (e.g., a surface of the support 1022). The contact between the bumper 1074 and the surgical table 1000 may generate a shock or impact force, which can be damped by the damper 1072. A shock or impact force can be generated, for example, when the arm cart 1050 contacts the surgical table 1000 at a high velocity or with a high momentum. The damper 1072 can damp away some of the shock by dissipating a portion of the kinetic energy of the shock. The arm cart 1050 can then be moved in a direction along an arrow G-G (e.g., moved toward the surgical table 1000) to engage the coupling member 1039 of the robotic arm 1030 with the coupling site 1046 of the surgical table 1000. When the arm cart 1050 is moved in the direction along arrow G-G, the bumper 1074 retracts in an opposite or inverse direction along arrow F-F. More specifically, the bumper 1074 displaces from the extended position, as shown in FIG. 10A, to the retracted position, as shown in FIG. 10B, due to the continued contact between the bumper 1074 and the surgical table 1000. As the bumper 1074 retracts, the damper 1072 can exert a counterforce that acts in a direction opposite to arrow F-F. This counterforce can act to limit a velocity or rate at which the arm cart 1050 is moved toward the surgical table 1000 in the direction along arrow G-G. For example, the damper 1072 may prevent the arm cart 1050 from moving toward the surgical table at velocities above a certain predefined velocity (e.g., velocities at which impact with the surgical table would damage the surgical table 1000, robotic arm 1030, coupling site 1046, and/or any other components).

The damper 1072 can be configured such that an impact load (e.g., a force applied over a short period of time) does not cause the bumper 1074 to move from its extended position to its retracted position but a sustained lower force (e.g., a smaller force applied over a longer period of time) can cause the bumper 1074 to move from its extended position to its retracted position. While the damping mechanism 1070 is depicted as retracting or displacing linearly along arrow F-F in FIGS. 10A and 10B, in other embodiments, the damping mechanism 1070 can be configured to rotate from an extended position to a retracted position. For example, the damping mechanism 1070 can be configured to rotate about a pivot point (e.g., rotate to an orthogonal position) to move aside and allow the coupling member 1039 to couple to the coupling site 1046. In still other embodiments, the damping mechanism 1070 can include an electrical damper or a magnetic damper that can be gradually switched off (e.g., can provide a gradually diminishing damping effect).

Although the arm cart 1050 is described as storing, deploying, and transferring one robotic arm 1030, in some embodiments the arm cart 1050 can store, deploy, and transfer a second robotic arm similarly as described above with respect to the robotic arm 1030. For example, both the robotic arm 1030 and a second robotic arm can be loaded onto the arm cart 1050 prior to transfer of either robotic arm to a surgical table. The arm cart 1050 can include one or more additional structures for supporting the second robotic arm, as well as a second damping mechanism similar in function to the damping mechanism 1070. After transferring the robotic arm 1030 to a first coupling site of a surgical table as described above, the arm cart 1050 can be moved, with the second robotic arm, via the base 1054 to another location near the surgical table. The second robotic arm can then be coupled and transferred to the surgical table and the arm cart 1050 can be moved away from the surgical table.

Figure 11A:
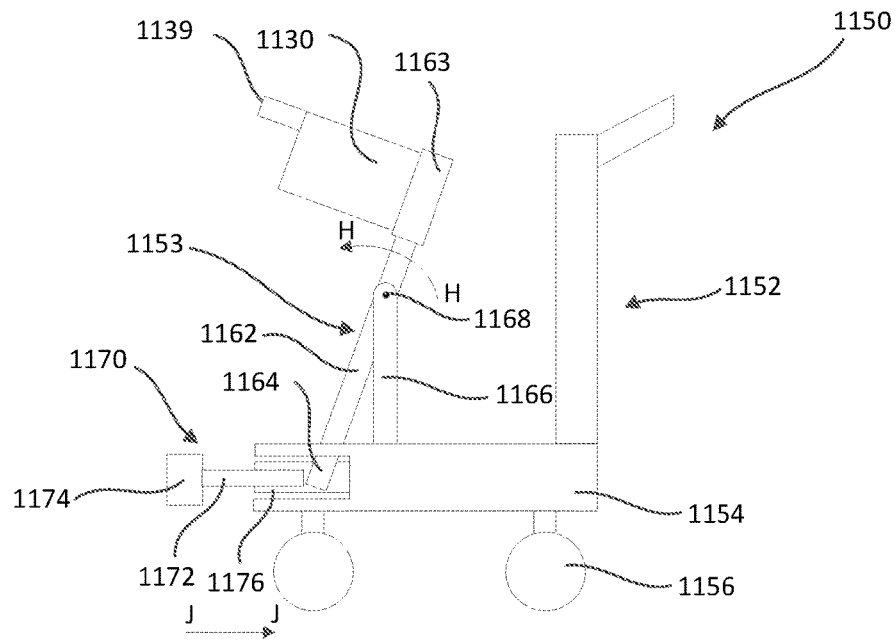
FIGS. 11A and 11B are schematic illustrations of another arm cart having a damping mechanism extending from a base of the cart in different configurations, according to an embodiment.
Figure 11B:
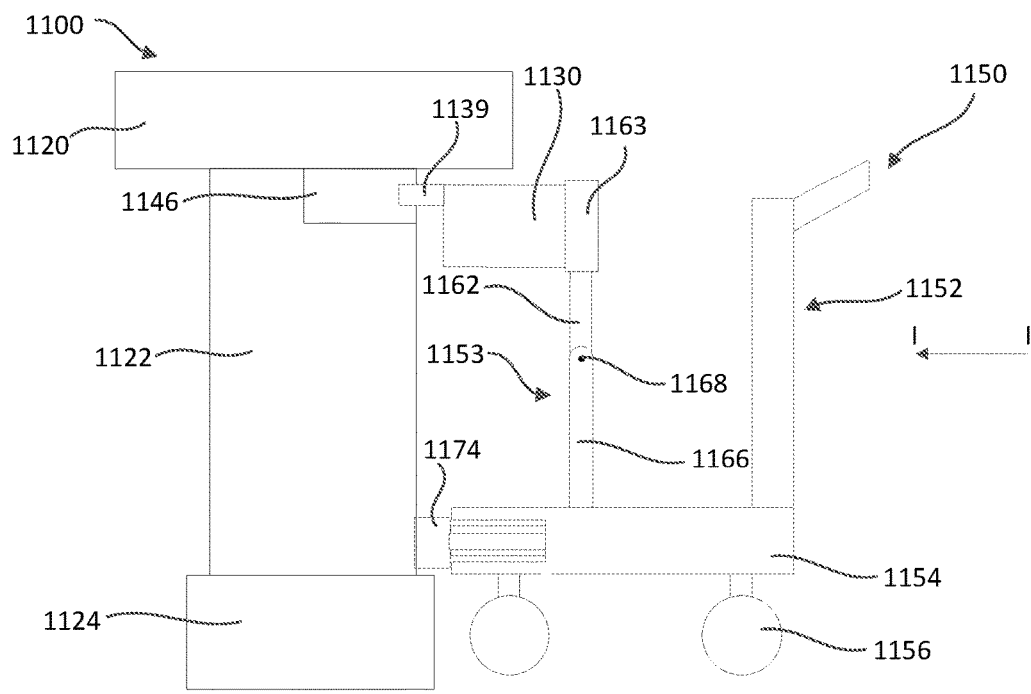

In some embodiments, a damping mechanism can also be configured to move a robotic arm from a first position in which a coupling member of the robotic arm is not engageable with a coupling site of a surgical table to a second position in which the coupling member is engageable with the coupling site. The damping mechanism can include an extension that moves linearly or rotationally to actuate the movement of the robotic arm. For example, as depicted in FIGS. 11A and 11B, an arm cart 1150 can have a damping mechanism 1170 that can engage with an arm support 1162 to move a robotic arm 1130.

The arm cart 1150 can be similar in structure and/or function to any of the arm carts described herein. For example, the arm cart 1150 includes an arm container 1152 and a base 1154. The arm container 1152 can be coupled to and extend upwardly from the base 1154. The base 1154 can be freely moveable on a support surface, such as, for example, a floor, between a first location remote from a surgical table 1100 and a second location adjacent to the surgical table 1100. For example, the base 1154 can be coupled to a number of wheels 1156, such as, for example, three or four wheels, such that the arm cart 1150 is moveably supported on the support surface.

The robotic arm 1130 can be similar in structure and/or function to any of the robotic arms described herein. For example, the robotic arm 1130 can include an arm coupling member 1139 (also referred to as a "coupler") that is configured to couple to a coupling site 1146 of the surgical table 1100. For schematic purposes, the robotic arm 1130 is shown generally in block form but, similar to other robotic arms described herein, can include one or more joints that can allow one or more segments of the robotic arm to move or rotate.

The arm cart 1150 can include an arm support 1153. As depicted in FIGS. 11A and 11B, the arm support 1153 can be configured to support the robotic arm 1130 above the base 1154 in multiple positions. The arm support 1153 includes an attachment site 1163 (or cradle) that is configured to releasably couple to the robotic arm 1130. The arm support 1153 also includes a pivotable member 1162 and a fixed member 1166. The pivotable member 1162 can be movably coupled to the fixed member 1166 via a pivot point 1168. The pivotable member 1162 can rotate about the pivot point 1168 to move the robotic arm 1130 between a first position, as shown in FIG. 11A, and a second position, as shown in FIG. 11B. When the robotic arm 1130 is in the first position, the coupling member 1139 of the robotic arm 1130 is positioned behind a front end of the arm cart 1150 and/or a front end of the damping mechanism 1170 (as further described below) and, therefore, is not engageable with the coupling site 1146 of the surgical table 1100. When the robotic arm 1130 is in the second position, the coupling member 1139 is engageable with the coupling site 1146.

The arm cart 1150 also includes the damping mechanism 1170. The damping mechanism 1170 may be operatively coupled to the base 1154 such that it is movable between an extended position, as shown in FIG. 11A, and a retracted position, as shown in FIG. 11B. In the extended position, the damping mechanism 1170 extends from the base 1154 beyond the coupling member 1139 such that the damping mechanism 1170 prevents the coupling member 1139 from coupling to the coupling site 1146 of the surgical table 1100. For example, as depicted in FIG. 11A, when the damping mechanism 1170 is in the extended position, the damping mechanism 1170 is configured to contact the surgical table 1100 before the coupling member 1139 can contact the coupling site 1146. When pressed against the surgical table 1100, the damping mechanism 1170 may retract along an arrow J-J to the retracted position, as shown in FIG. 11A. When the damping mechanism 1170 moves from the extended position to the retracted position, a portion (e.g., a shaft 1172 of the damping mechanism 1170) contacts an end 1164 of the pivotable member 1162 of the arm support 1153 and causes the pivotable member 1162 to rotate about the pivot point 1168 along an arrow H-H. The rotation of the pivotable member 1162 along arrow H-H moves the robotic arm 1130 from the first position to the second position such that the coupling member 1139 is positioned to engage with the coupling site 1146 of the surgical table, as shown in FIG. 11B. The damping mechanism 1170 can include a bumper 1174 that is coupled to a shaft 1172. The shaft 1172 may be coupled to or form part of a mechanical damper 1176, such as, for example, a spring and/or a dashpot.

The surgical table 1100, as depicted in FIG. 11B, can be similar in structure and/or function to any of the surgical tables described herein. For example, the surgical table 1100 may have a table top 1120, a support or pedestal 1122, and a base 1124. The support 1122 can support the table top 1120 at a suitable height above the floor. The surgical table 1100 can also include a coupling member or coupling site 1146 that can couple with the coupling member 1139 of the robotic arm 1130. Although the coupling site 1146 is shown as being disposed below the table top 1120, in some embodiments, the coupling site 1146 can be disposed to the side or on the top of the table top 1120.

In use, the robotic arm 1130 can be loaded onto the arm cart 1150. The arm cart 1150 can be moved from a location remote from the surgical table 1100 to a location proximate to the surgical table 1100. When the arm cart 1150 is moved to the location proximate to the surgical table 1100, the bumper 1174 of the damping mechanism 1170 may contact a portion of the surgical table 1100 (e.g., a surface of the support 1122). The contact between the bumper 1174 and the surgical table 1100 may generate a shock or impact force, which can be damped by the damper 1176. A shock or impact force can be generated, for example, when the arm cart 1150 contacts the surgical table 1100 at a high velocity or with a high momentum. The damper 1176 can damp away some of the shock by dissipating a portion of the kinetic energy of the shock. The arm cart 1150 can then be moved in a direction along an arrow I-I (e.g., moved toward the surgical table 1100) to engage the coupling member 1139 of the robotic arm 1130 with the coupling site 1146 of the surgical table 1100. When the arm cart 1150 is moved in the direction along arrow I-I, the bumper 1174 retracts in an opposite or inverse direction along arrow J-J. More specifically, the bumper 1174 displaces from the extended position, as shown in FIG. 11A, to the retracted position, as shown in FIG. 11B, due to the continued contact between the bumper 1174 and the surgical table 1100. As the bumper 1174 retracts, the damper 1176 can exert a counterforce that acts in a direction opposite to arrow J-J. This counterforce can act to limit a velocity or rate at which the arm cart 1150 is moved toward the surgical table 1100 in the direction along arrow J-J. As the bumper 1174 retracts, the shaft 1172 also contacts the end 1164 of the pivotable member 1162, which causes the pivotable member 1162 to pivot and move the robotic arm 1130 from the first position, as shown in FIG. 11A, to the second position, as shown in FIG. 11B.

Although the arm cart 1150 is described as storing, deploying, and transferring one robotic arm 1130, in some embodiments the arm cart 1050 can store, deploy, and transfer a second robotic arm similarly as described above with respect to the robotic arm 1030. For example, both the robotic arm 1130 and a second robotic arm can be loaded onto the arm cart 1150 prior to transfer of either robotic arm to a surgical table. The arm cart 1050 can include a second arm support, similar to the arm support 1153, for supporting the second robotic arm, as well as a second damping mechanism, similar to the damping mechanism 1170. After transferring the robotic arm 1130 to a first coupling site of a surgical table as described above, the arm cart 1150 can be moved, with the second robotic arm, via the base 1154 to another location near the surgical table. The second robotic arm can then be coupled and transferred to the surgical table and the arm cart 1150 can be moved away from the surgical table.

Figure 12:
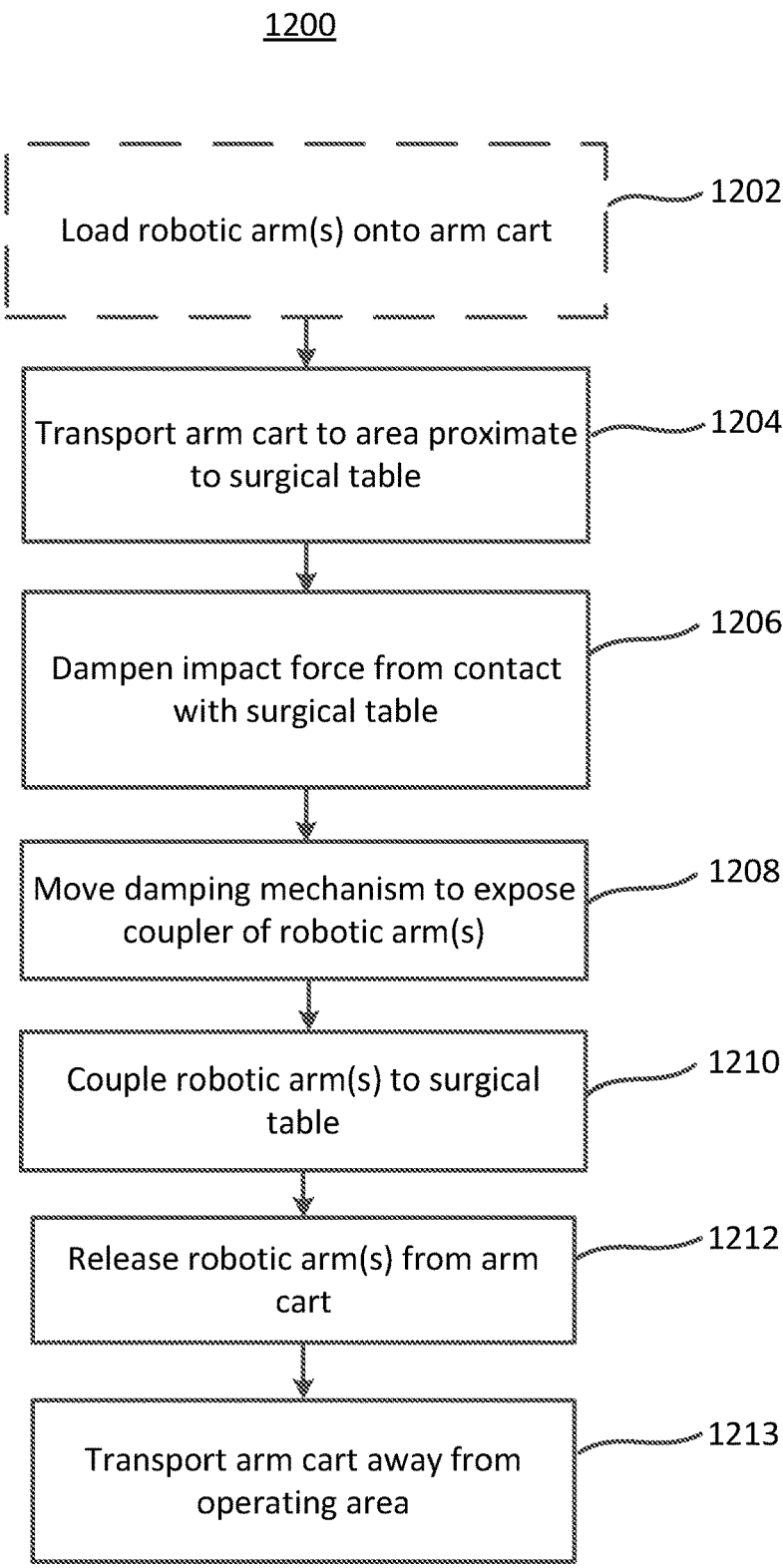
FIG. 12 is a flowchart of a method of using an arm cart to transfer robotic arms to a surgical table, according to an embodiment.

FIG. 12 is a flow chart of a method 1200 of transporting and transferring surgical robotic arms to a surgical table using a surgical robotic arm cart, such as any of the arm carts described herein. Similar to the method 500, the method 1200 may optionally include loading one or more robotic arms onto an arm cart, at 1202. As 1204, the arm cart is transported to an area proximate to a surgical table. At 1206, a damping mechanism of the arm cart (e.g., the damping mechanism 1070 or the damping mechanism 1170) may contact a portion of the surgical table. The arm cart via the damping mechanism can damp or absorb impact or shock forces that are imparted to the arm cart due to the contact between the damping mechanism and the arm cart. The damping mechanism can be disposed on or form a part of a base or an arm support of the arm cart. By absorbing the shock forces, the damping mechanism can prevent damage to a robotic arm and/or the surgical table. For example, the damping mechanism can extend from the arm cart such that it contacts the surgical table before the robotic arm or another portion of the arm cart contacts the surgical table. Thus, if the arm cart approaches the surgical table at a high velocity, the damping mechanism can absorb any shock that results from the initial contact between the arm cart and the surgical table. Portions of the damping mechanism that contact the surgical table (e.g., the bumper 1074 or the bumper 1174) can be made of shock-absorbing material or pliant material such that those portions do not damage the surgical table during the initial contact. The damping mechanism can also include a damper, such as a mechanical, electrical, or magnetic damper.

At 1208, the damping mechanism can be moved to expose a coupler of a robotic arm. For example, the damping mechanism can be moved aside such that the coupler can be engaged with a coupling site of the surgical table. The damping mechanism can be moved linearly, rotationally, or some combination thereof. In some embodiments, movement of the damping mechanism can also result in movement of the robotic arm into a position that permits the coupler to engage with the coupling site, such as described with reference to the arm cart 1150. At 1210, the robotic arm can be coupled to the surgical table. For example, the coupler of the robotic arm can be releasably coupled to the coupling site of the surgical table. At 1212, the robotic arm is released from the arm cart. At 1214, the arm cart is transported away from the area proximate to the surgical table.

In some embodiments, if a second robotic arm has been loaded onto the arm cart (or is stored in the arm cart), the arm cart can couple a first robotic arm to the surgical table, release the first robotic arm from the arm cart, and be transported to a location adjacent to another portion of the surgical table. The second robotic arm can then be coupled to the surgical table. The second robotic arm can be released from the arm cart and the arm cart can be transported away from the operating area.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A cart for a surgical robotic arm having a coupler releasably coupleable to a coupling site on a surgical table, the cart comprising:
    a base freely moveable relative to a surgical table; and
    an arm support coupled to the base and releasably coupleable to the arm, the arm support configured to support the arm in a position in which a portion of the arm is exposed to contact the surgical table, the arm support including;
        an engagement feature engageable with a portion of the arm; and
        a damping mechanism configured to damp an impact force imparted to the arm by the surgical table when the base is moved to a location proximate to the surgical table and the portion of the arm contacts the surgical table.

2. The cart of claim 1, wherein the position in which the portion of the arm is exposed to contact the surgical table is a deployed position, the arm support further configured to permit movement of the arm between a stored position in which the portion of the arm is not exposed to contact the surgical table and the deployed position.

3. The cart of claim 2, wherein the arm support includes a joint configured to rotate about a pivot point between a first position in which the arm is in the stored position and a second position in which the arm is in the deployed position.

4. The cart of claim 3, further comprising a mechanical mechanism configured to assist in rotating the joint between the first position and the second position, the mechanical mechanism including at least one of a spring and a pressure cylinder.

5. The cart of claim 1, wherein the damping mechanism includes at least one of a spring and a dashpot.

6. The cart of claim 1, wherein the coupler is configured to slide into an opening formed in the coupling site, and wherein the damping mechanism is configured to control a rate at which the coupler slides into the opening.

7. The cart of claim 1, wherein the engagement feature includes a ball component configured to releasably engage with a detent component disposed on the arm.

8. A cart for a surgical robotic arm having a coupler releasably coupleable to a coupling site on a surgical table, the cart comprising:
    a base freely moveable relative to a surgical table; and
    an arm support coupled to the base and releasably coupled to the arm,
    the arm support configured to support the arm such that a portion of the arm is exposed to contact the surgical table;

the arm support configured to bend to damp an impact force imparted to the arm by the surgical table when the base is moved to a location proximate to the surgical table and the arm contacts the surgical table.

9. The cart of claim 8, wherein the arm support damps the impact force by bending to permit the arm to translate and rotate relative to the base when the arm contacts the surgical table.

10. The cart of claim 8, wherein the arm support is flexible in a plane transverse to a longitudinal axis of the arm support and rigid along the longitudinal axis of the arm support.

11. The cart of claim 8, wherein the arm support is formed of a material having a low elastic modulus and a high tensile strength.

12. The cart of claim 8, wherein the arm support includes a joint configured to permit translation and rotation of the arm about at least one axis.

13. The cart of claim 12, wherein the joint includes a flexible bellows.

14. The cart of claim 8, further comprising a stop configured to engage the arm support and limit a degree of bending of the arm support.

15. A cart for a surgical robotic arm having a coupler releasably coupleable to a coupling site on a surgical table, the cart comprising:
a base freely moveable on a support surface relative to a surgical table; and
a damping mechanism coupled to the base and movable between an extended position in which the damping mechanism prevents the coupler from coupling to the coupling site and a retracted position in which the damping mechanism permits the coupler to couple to the coupling site;
the damping mechanism configured to contact the surgical table when the base is moved to a location proximate to the surgical table and the damping mechanism is in the extended position,
the damping mechanism configured to damp an impact force imparted to the damping mechanism by the surgical table when the damping mechanism contacts the surgical table,
the damping mechanism movable from the extended position to the retracted position when the cart is moved toward the surgical table at a velocity less than a predefined velocity.

16. The cart of claim 15, wherein the damping mechanism includes:
a bumper component configured to contact the surgical table; and
an energy-absorbing component coupled to the bumper and the cart and configured to damp the impact force.

17. The cart of claim 16, wherein the energy-absorbing component comprises at least one of a spring and a dashpot.

18. The cart of claim 15, wherein the damping mechanism is configured to linearly displace when moving between the extended position and the retracted position.

19. The cart of claim 15, wherein the damping mechanism is configured to rotate when moving between the extended position and the retracted position.

20. The cart of claim 15, further comprising an arm support releasably coupled to the arm and configured to move the arm between a first position in which the coupler is not engageable with the coupling site and a second position in which the coupler is engageable with the coupling site,
wherein the arm support moves the arm from the first position to the second position when the damping mechanism moves from the extended position to the retracted position.

* * * * *